(12) United States Patent
Sundararajan et al.

(10) Patent No.: US 7,442,339 B2
(45) Date of Patent: Oct. 28, 2008

(54) MICROFLUIDIC APPARATUS, RAMAN SPECTROSCOPY SYSTEMS, AND METHODS FOR PERFORMING MOLECULAR REACTIONS

(75) Inventors: Narayanan Sundararajan, San Francisco, CA (US); Lei Sun, Santa Clara, CA (US); Yuegang Zhang, Cupertino, CA (US); Xing Su, Cupertino, CA (US); Selena Chan, San Jose, CA (US); Tae-Woong Koo, Cupertino, CA (US); Andrew A. Berlin, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 430 days.

(21) Appl. No.: 10/815,264

(22) Filed: Mar. 31, 2004

(65) Prior Publication Data
US 2005/0221333 A1    Oct. 6, 2005

(51) Int. Cl.
*G01N 21/65*    (2006.01)
*G01J 3/44*    (2006.01)
*G01N 33/48*    (2006.01)

(52) U.S. Cl. ............... 422/82.05; 356/301; 422/50; 422/81; 422/100; 436/43; 436/52; 436/86; 436/94; 436/171

(58) Field of Classification Search ............ 422/50, 422/81–82, 100–102, 82.05; 436/43, 52, 436/86–90, 94, 171; 356/301
See application file for complete search history.

(56) References Cited

U.S. PATENT DOCUMENTS

| | | | | |
|---|---|---|---|---|
| 4,893,886 A | | 1/1990 | Ashkin et al. ............ 350/1.1 |
| 5,100,627 A | | 3/1992 | Buican et al. ............ 422/108 |
| 5,304,487 A | * | 4/1994 | Wilding et al. ............ 435/29 |
| 5,427,663 A | * | 6/1995 | Austin et al. ............ 204/549 |
| 5,587,128 A | * | 12/1996 | Wilding et al. ............ 422/50 |
| 5,620,857 A | * | 4/1997 | Weetall et al. ............ 435/7.1 |
| 5,674,743 A | | 10/1997 | Ulmer ............ 435/287 |
| 5,776,674 A | * | 7/1998 | Ulmer ............ 435/6 |
| 6,049,380 A | | 4/2000 | Goodwin et al. ............ 356/317 |
| 6,083,761 A | * | 7/2000 | Kedar et al. ............ 506/30 |
| 6,159,749 A | * | 12/2000 | Liu ............ 436/527 |
| 6,514,767 B1 | | 2/2003 | Natan ............ 436/166 |
| 6,602,702 B1 | * | 8/2003 | McDevitt et al. ............ 435/288.7 |

(Continued)

FOREIGN PATENT DOCUMENTS

JP    2003-189852    *    7/2003

OTHER PUBLICATIONS

Li, L.-Q. et al, Applied Optics 1995, 34, 3208-3217.*

(Continued)

*Primary Examiner*—Arlen Soderquist
(74) *Attorney, Agent, or Firm*—Darby & Darby PC

(57) ABSTRACT

Disclosed herein are methods, apparatuses, and systems for performing nucleic acid sequencing reactions and molecular binding reactions in a microfluidic channel. The methods, apparatuses, and systems can include a restriction barrier to restrict movement of a particle to which a nucleic acid is attached. Furthermore, the methods, apparatuses, and systems can include hydrodynamic focusing of a delivery flow. In addition, the methods, apparatuses, and systems can reduce non-specific interaction with a surface of the microfluidic channel by providing a protective flow between the surface and a delivery flow.

21 Claims, 6 Drawing Sheets

U.S. PATENT DOCUMENTS

| | | | |
|---|---|---|---|
| 6,696,022 B1* | 2/2004 | Chan et al. | 422/99 |
| 6,863,406 B2* | 3/2005 | Grier et al. | 359/614 |
| 2002/0150938 A1* | 10/2002 | Kneipp et al. | 435/6 |
| 2002/0160363 A1* | 10/2002 | McDevitt et al. | 435/6 |
| 2002/0181837 A1* | 12/2002 | Wang et al. | 385/16 |
| 2003/0159999 A1* | 8/2003 | Oakey et al. | 210/695 |
| 2003/0186426 A1* | 10/2003 | Brewer et al. | 435/287.2 |
| 2003/0187237 A1* | 10/2003 | Chan et al. | 536/22.1 |
| 2003/0198575 A1* | 10/2003 | Noda et al. | 422/100 |
| 2004/0012778 A1* | 1/2004 | Li et al. | 356/301 |
| 2005/0048581 A1* | 3/2005 | Chiu et al. | 435/7.1 |

OTHER PUBLICATIONS

Schecker, J. A. et al, SPIE 1995, 2386, 4-12.*
Wang, W. et al, SPIE 1996, 2629, 70-77.*
Hoyer, C. et al, SPIE 1996, 2928, 188-199.*
Dorre, K. et al, Bioimaging 1997, 5, 139-152.*
Machara, N. P. et al, Bioimaging 1998, 6, 33-42.*
Fiedler, S. et al, Analytical Chemistry 1998, 70, 1909-1915.*
Kneipp, K. et al, Physical Review E 1998, 57, R6281-R6284.*
Andersson, H. et al, Sensors and Actuators B 2000, 67, 203-208.*
Hsieh, T.-M. et al, SPIE 2000, 4082, 232-240.*
Wuite, G. J. L. et al, Biophysical Journal 2000, 79, 1155-1167.*
Yin, Y. et al, Journal of the American Chemical Society 2001, 123, 8718-8729.*
Ishikawa, M. et al, Journal of Biological Physics 2002, 28, 573-585.*
Houlne, M. P. et al, Analytical Chemistry 2002, 74, 4311-4319.*
Soni, G. V. et al, Current Science 2002, 83, 1464-1470.*
Werner, J. H. et al, Journal of Biotechnology 2003, 102, 1-14.*
Kneipp, K. et al, Chemical Abstracts 2003 abstract 139:156658.*
Sischka, A. et al, Review of Scientific Instruments 2003, 74, 4827-4831.*
Terray, A. et al, Applied Physics Letters 2002, 81, 1555-1557.*
Park, B. H. et al, SPIE 2003, 5116, 303-313.*
Doering, et al., "Spectroscopic Tags Using Dye-Embedded Nanoparticles and Surface—Enhanced Raman Scattering", *Analytical Chemistry*, :5-9.
Knight, et al., "Hydrodynamic Focusing on a Silicon Chip: Mixing Nanoliters in Microseconds", *Am Phy Soc.* 80(17):3683-3866 (1998).
Mulvaney, et al., "Glass-Coated, Analyte-Tagged Nanoparticles: A New Tagging System Based on Detection with Surface-Enhanced Raman Scattering", *Am Chem Soc.* 19:4784-4790 (2003).
Takayama, et al., "Subcellular Positioning of Small Molecules", Nat. 411:1016 (2001).
Woolley, et al., Deposition and Characterization of Extended Single-Stranded DNA Molecules on Surfaces, *Lett* 1(7):345-348 (2001).

* cited by examiner

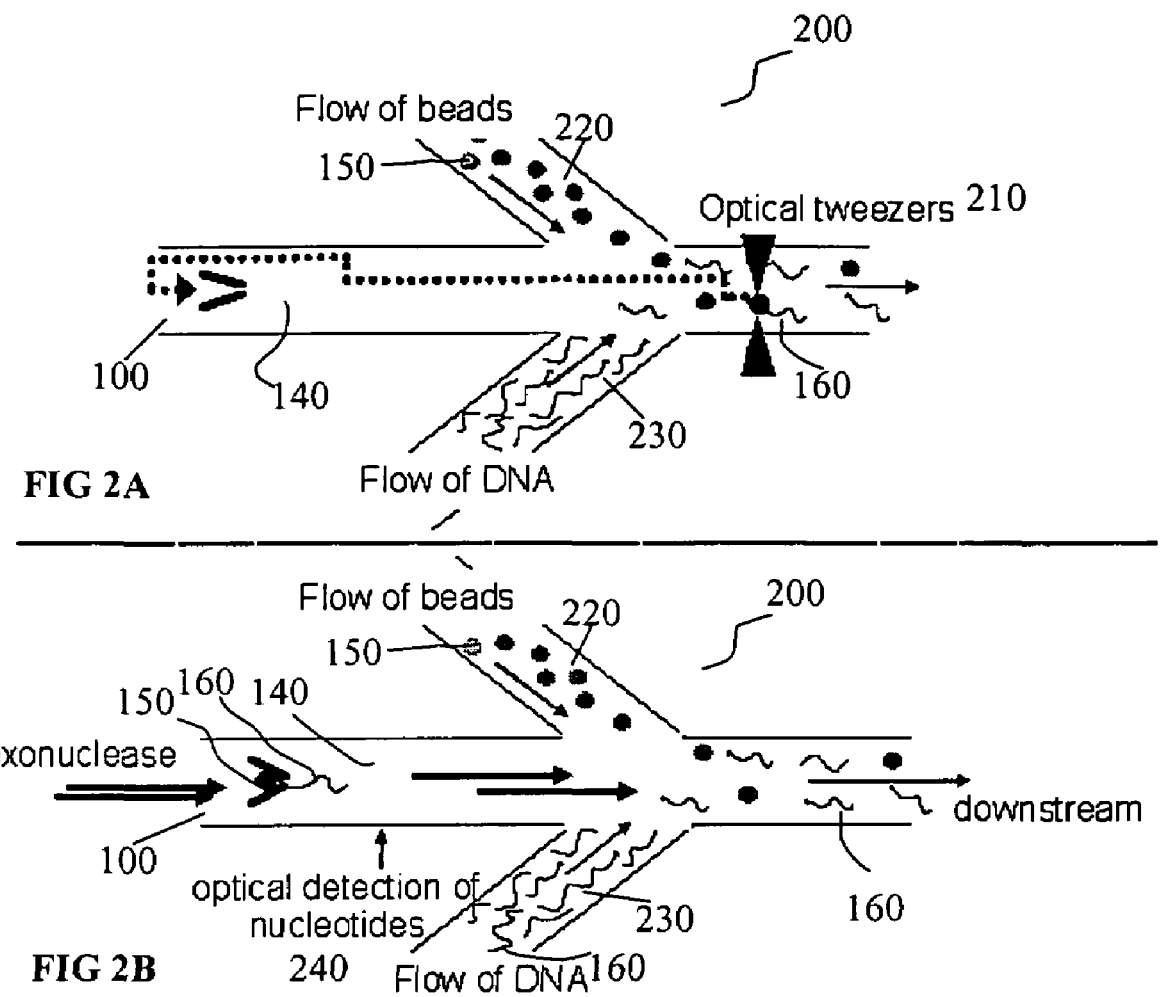

Fluidic Alignment

Fluidic Alignment
exposes the ends of the molecules

Reactants
(phosphoramidites)
have better access to
the end of the DNA,
thus give better yield.

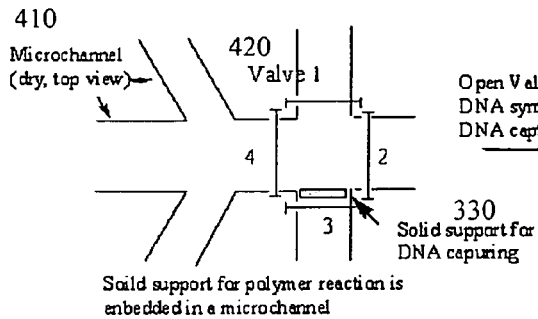

FIG. 4A
Solid support for polymer reaction is embedded in a microchannel

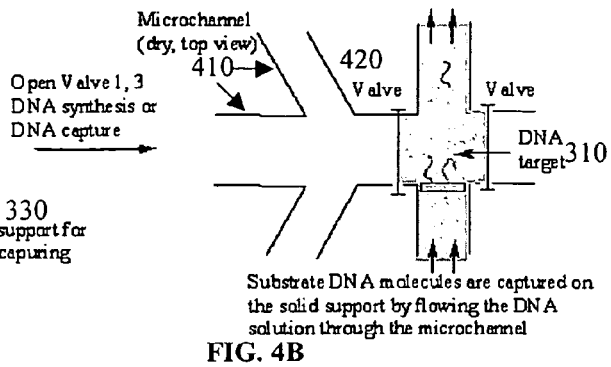

FIG. 4B
Substrate DNA molecules are captured on the solid support by flowing the DNA solution through the microchannel

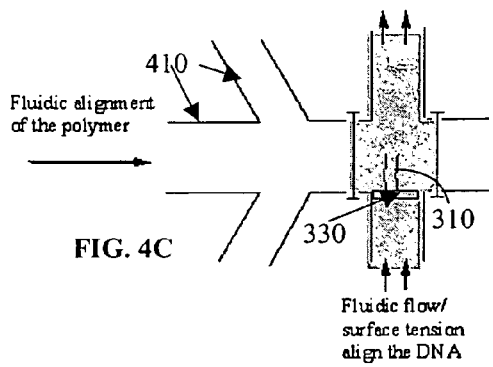

FIG. 4C
Fluidic alignment of the polymer / Fluidic flow/surface tension align the DNA

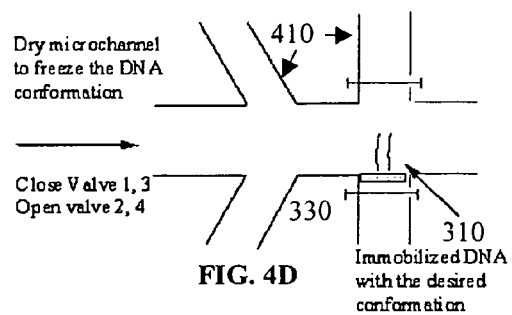

FIG. 4D
Immobilized DNA with the desired conformation

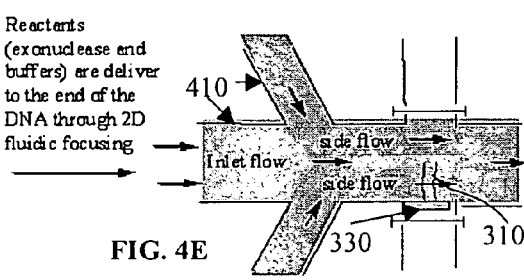

FIG. 4E
Reactants (exonuclease and buffers) are delivered to the end of the DNA through 2D fluidic focusing

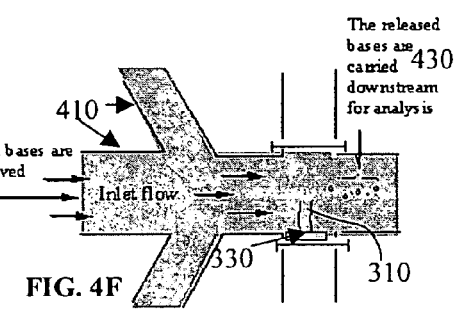

FIG. 4F
The released bases are carried downstream for analysis

Only the selected region (50nm, ~150 bases from the end) of the DNA molecules can be digested. Hence the reaction is synchronized at ~150 bases.

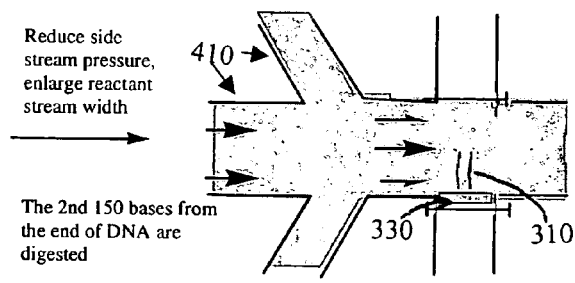

FIG. 4G
Reduce side stream pressure, enlarge reactant stream width
The 2nd 150 bases from the end of DNA are digested

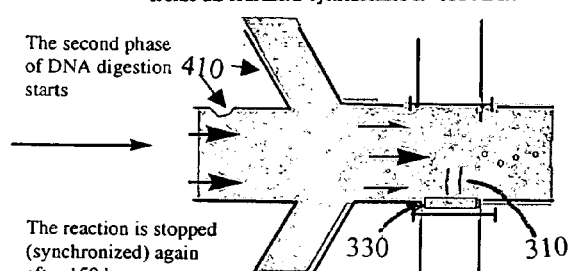

FIG. 4H
The second phase of DNA digestion starts
The reaction is stopped (synchronized) again after 150 bases

MICROFLUIDIC APPARATUS, RAMAN SPECTROSCOPY SYSTEMS, AND METHODS FOR PERFORMING MOLECULAR REACTIONS

BACKGROUND OF THE INVENTION

1. Field of the Invention

The present invention relates generally to devices, systems, and methods for performing molecular reactions, and more specifically to microfluidic devices, systems, and methods for performing molecular reactions.

2. Background Information

Determination of the entire sequence of the human genome has provided a foundation for identifying the genetic basis of diseases such as cancer, cystic fibrosis, sickle cell anemia and muscular dystrophy. However, a great deal of work remains to be done to identify the genetic variations associated with each disease and to develop more sensitive and accurate tests for these diseases. This development would be accelerated greatly if efficiency and product yields of present methods were improved.

Current methods for determining nucleic acid sequence information are laborious, expensive, and inefficient. This is indicative of the shortcomings of many current molecular reactions used in biotechnology, such as DNA synthesis or carbon nanotube production, which provide a low reaction yield of the desired product. In addition, many side reactions occur in macromolecule reactions that yield undesirable products. Finally, lack of synchronization in multi-molecule polymer reactions (e.g. exonuclease DNA sequencing) results in inaccurate results.

To attempt to overcome their shortcomings, current methods usually require a large excess of reagent, which results in more side reaction and higher cost. Furthermore, in many cases reactions must be performed in multiple steps and require nucleic acid manipulation. For example, a desired "block" of a macromolecule is synthesized and then linked (i.e. ligated) to form a final product (e.g. insert a modified gene into a plasmid). This results in inefficient methods with relatively low yield and low product purity.

BRIEF DESCRIPTION OF THE DRAWINGS

FIGS. 2A and 2B illustrate an exemplary system and method provided herein, wherein a bead 150 with an attached nucleic acid molecule 160 assembled downstream of a detection unit, is captured by optical tweezers 210, transported and released upstream of a restriction barrier 140.

FIG. 3A illustrates fluidic alignment. FIG. 3B illustrates exposure of an end (i.e. terminus) of the nucleic acid molecules 310. FIG. 3C illustrates addition of nucleotide subunits 320 to the nucleic acid molecule 310.

FIGS. 4A-4H provides a series of schematic diagrams illustrating exonuclease nucleic acid sequencing with fluidic alignment and fluidic focusing.

DETAILED DESCRIPTION OF THE INVENTION

Figure 1:
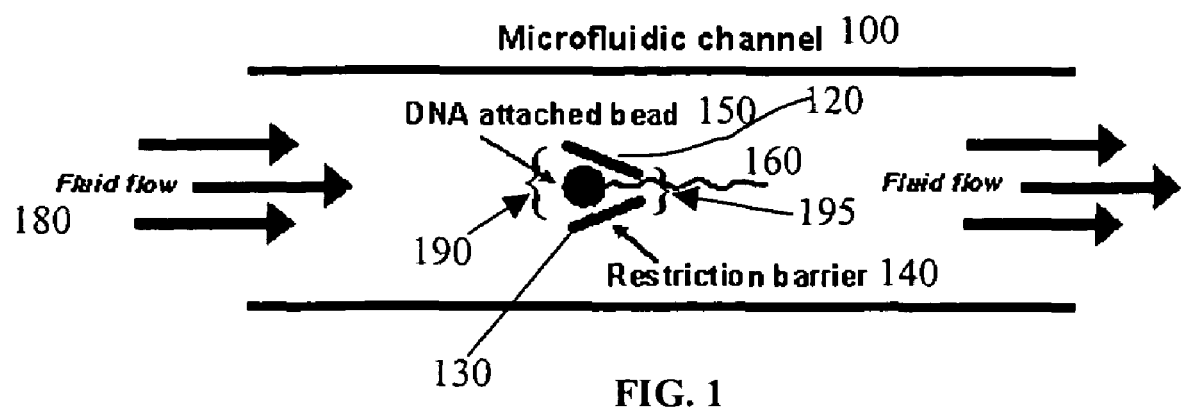
FIG. 1 illustrates confinement in a restriction barrier 140 of a bead 150 with an attached nucleic acid molecule 160 in a microfluidic channel 100.

The invention generally provides improved apparatuses, systems and methods for performing biomolecular reactions in a microfluidic device. In one group of related embodiments, referred to herein as "the nucleic acid capture" embodiments, the disclosed systems, apparatus, and methods provide for the capture of a single nucleic acid molecule in a microfluidic channel upstream from an optical detector. These embodiments allow sequential detection of one or more nucleotides released from a nucleic acid molecule. Accordingly, the disclosed methods, systems and apparatus are of use for the rapid, automated sequencing of at least a portion of a nucleic acid molecule.

Methods for isolating single nucleic acid molecules on a solid support and manipulation of these molecules with optical tweezers have been developed. However, the lasers used by optical tweezers could potentially affect optical detection methods such as Raman spectroscopy. Furthermore, the integration of optical tweezers and a Raman detector is limited by the field of view when using the same microscope objective (~100 microns for a 20X objective). The use of two microscope objectives directly adjacent to each other further separates the optical tweezers component from the Raman detection on a scale of several centimeters. However, the use of two microscope objectives placed on top and below the substrate requires that the material of the microfluidic channel is optically transparent and has the same transmission properties from a top and bottom layer.

The methods provided herein overcome these problems by facilitating the isolation and manipulation of single nucleic acid molecules without interfering with optical detection of the nucleic acid molecule or a single nucleotide. Methods can be performed in the microfluidic channel to functionalize a solid support, e.g., a particle such as a bead, with the single nucleic acid molecule. A single bead with a single nucleic acid molecule attached, can be transported and released upstream of a detector using optical tweezers, for example. The optical tweezers are typically a gradient force optical trap, such as a single-beam gradient force optical trap, that captures the single particle downstream from the laser beam.

The released bead can then flow downstream and either become trapped in a restriction barrier or attached to a surface. Once the bead is confined, the optical tweezers can be removed so that they do not interfere with an optical detector downstream. Single nucleotides can be cleaved from the bead using an exonuclease, for example. The single nucleotides are then detected using spectroscopic methods such as surface enhanced Raman spectroscopy (SERS). The inclusion of a restriction barrier in a microfluidic channel and the immobilization of an optically transported bead, allows removal of the optical tweezers from the optical path of a detection device, thereby preventing interference from the additional light source of the optical tweezers close to the collection volume of the detector.

Accordingly, presented herein is a system that includes a surface enhanced Raman spectroscopy (SERS) detection unit and a first channel in optical communication with the SERS detection unit, wherein the first channel contains a restriction barrier to restrain movement of a single particle with an attached nucleic acid molecule. The SERS detection unit typically includes a detection light source, typically a laser light source, for irradiating a molecule, and a detection unit for detecting Raman emission from the irradiated molecule.

These systems are used to analyze the nucleic acid molecule attached to the surface of the particle. For example, the system can be used to perform a method to determine a nucleotide sequence of a nucleic acid molecule. The method includes restraining movement of a single nucleic acid molecule attached to a single particle in a first channel that includes a restriction barrier, by capturing the single particle in the restriction barrier. The captured nucleic acid molecule is then contacted with an agent that removes nucleotides, e.g., an exonuclease, to release a terminal nucleotide which is then detected using surface enhanced Raman spectroscopy (SERS). Typically, a first released nucleotide and a second released nucleotide are identified after associating the released nucleotides with a SERS-active surface such as a SERS substrate or a metal nanoparticle in solution, irradiating the released nucleotides with a detection laser beam and measuring Raman emission from the irradiated nucleotides. Additional released nucleotides can be detected. By detecting the released nucleotides a nucleotide sequence of the nucleic acid molecule is determined.

In other aspects, a nucleic acid molecule restrained in the restriction barrier can be analyzed using methods other than by exonuclease treatment in a sequencing reaction. For example, the system can be used to amplify a nucleic acid molecule attached to the surface of the particle using known amplification methods, such as the polymerase chain reaction. Furthermore, the trapped nucleic acid molecule can be analyzed by hybridization using probes, such as fluorescently labeled and/or Raman-labeled probes. In certain aspects, multiple smaller nucleic acid probes with different labels can be contacted with the restrained nucleic acid molecule. Each nucleic acid probe identifies a nucleotide sequence to which it binds. Therefore, binding of the probes to the restrained nucleic acid molecule identifies the presence of a nucleotide sequence in the restrained nucleic acid molecule and provides and provides a type of barcode.

In another embodiment, an apparatus is provided for performing sequencing methods. The apparatus includes a surface enhanced Raman spectroscopy (SERS) detection unit; a first channel in optical communication with the detection unit, and a restriction barrier upstream of the detection unit to restrain movement of the particle. The apparatus can optionally include a second channel in fluid communication with the first channel, forming a junction with the first channel downstream from the SERS detection unit. Furthermore, the apparatus optionally includes optical tweezers having a laser capable of moving from a starting position downstream from the SERS detection unit, and typically downstream from the first channel and the second channel to a position upstream from the SERS detection unit. Alternatively, the SERS detection unit can have a moveable stage to effect the same transport of a nucleic acid molecule from downstream of the detection unit to upstream of the detection unit. The apparatus can further include a third channel, wherein the third channel is in fluid communication with the second channel and wherein the third channel and the first channel form a junction downstream of the detection unit. The optical tweezers are typically a gradient force optical trap that captures a single particle.

In another embodiment, provided herein is an apparatus including, a first channel including a restriction barrier comprising a first angled wall and a second angled wall positioned relative to the first angled wall to form a first opening at least 1 micron in width or diameter and a second opening less than 10 microns in width or diameter, wherein the first opening has a greater width or diameter than the second opening. In certain aspects, the second opening is less than 1 micron in width or diameter. The apparatus can further include a light source and a detector to detect a surface enhanced Raman spectroscopy emission of a molecule irradiated by the light source. In these aspects the first channel is in optical communication with the light source and the detector.

In another embodiment, provided herein is a system including:
a) a light source
b) a detector to detect a surface enhanced Raman spectroscopy emission of a molecule irradiated by the light source; and
c) a first channel in optical communication with the light source and the detector, wherein the first channel includes a restriction barrier comprising a plurality of angled walls to restrain movement of a single particle upstream of light emitted by the light source.

In yet another embodiment, a method is provided to detect a nucleotide, that includes restraining movement of a particle that includes a nucleic acid molecule attached to its surface, using a restriction barrier located within a first channel; contacting the nucleic acid molecule with an exonuclease to release the nucleotide from the nucleic acid molecule; and identifying the released nucleotide using surface enhanced Raman spectroscopy (SERS). SERS is typically performed by irradiating the released nucleotide with a detection laser beam and measuring Raman emission from the irradiated nucleotide.

Also provided is a method to restrain movement of a single nucleic acid molecule immobilized on a single particle in a first channel by capturing the single particle in a restriction barrier. In one aspect, the restriction barrier includes a first angled wall and a second angled wall positioned relative to the first angled wall to capture the single particle having the surface with the attached nucleic acid molecule. As discussed, in one aspect the first angled wall and the second angled are spaced apart to allow a nucleotide, the nucleic acid molecule, and/or a protein to pass through the restriction barrier. Since the nucleic acid molecule for example, is attached to the particle, it is held within the restraint by the particle. However, when a biomolecule such as a nucleotide, is released from the particle, it is released from the restraint. Since the captured single nucleic acid molecule is accessible to other reactants, it can be used in biochemical reactions, such as exonuclease reactions, to detect a terminal nucleotide of the captured nucleic acid molecule, which is useful for determining at least partial nucleic acid sequence information regarding the captured nucleic acid molecule.

As used herein, "a" or "an" may mean one or more than one of an item.

"Nucleic acid" encompasses DNA, RNA, single-stranded, double-stranded or triple stranded and any chemical modifications thereof, although single-stranded nucleic acids are preferred. Virtually any modification of the nucleic acid is contemplated. As used herein, a single stranded nucleic acid may be denoted by the prefix "ss", a double stranded nucleic acid by the prefix "ds", and a triple stranded nucleic acid by the prefix "ts."

A "nucleic acid" may be of almost any length, from 10, 20, 30, 40, 50, 60, 75, 100, 125, 150, 175, 200, 225, 250, 275, 300, 400, 500, 600, 700, 800, 900, 1000, 1500, 2000, 2500, 3000, 3500, 4000, 4500, 5000, 6000, 7000, 8000, 9000, 10,000, 15,000, 20,000, 30,000, 40,000, 50,000, 75,000, 100,000, 150,000, 200,000, 500,000, 1,000,000, 1,500,000, 2,000,000, 5,000,000 or even more bases in length, up to a full-length chromosomal DNA molecule.

A "nucleoside" is a molecule comprising a base (A, C, G, T or U) covalently attached to a pentose sugar such as deoxyribose, ribose or derivatives or analogs of pentose sugars.

A "nucleotide" refers to a nucleoside further comprising at least one phosphate group covalently attached to the pentose sugar. In some embodiments, the nucleotides are ribonucleoside monophosphates or deoxyribonucleoside monophosphates although in certain embodiments it is anticipated that nucleoside diphosphates or triphosphates could be produced. In other embodiments, nucleosides may be released from the nucleic acid molecule and detected as discussed below. It is contemplated that various substitutions or modifications may be made in the structure of the nucleotides, so long as they are still capable of being released from the nucleic acid by a deconstruction reagent. For example, in certain embodiments the ribose or deoxyribose moiety may be substituted with another pentose sugar or a pentose sugar analog. In other embodiments, the phosphate groups may be substituted by various analogs such as fluorescent labels.

Nucleic acid molecules to be sequenced can be prepared by any technique known in the art. In certain embodiments, the nucleic acids are naturally occurring DNA or RNA molecules. Virtually any naturally occurring nucleic acid may be prepared and sequenced by the disclosed methods including, without limit, chromosomal, mitochondrial and chloroplast DNA and ribosomal, transfer, heterogeneous nuclear and messenger RNA.

As used herein, the term "specific binding pair member" refers to a molecule that specifically binds or selectively hybridizes to, or interacts with, another member of a specific binding pair. Specific binding pair members include, for example a receptor and a ligand, or an antigen and an antibody. For example, the first specific binding pair member can be a protein, such as an antibody molecule, or fragment thereof, and the second specific binding pair member can be a biomolecule, such as a protein, that includes an epitope recognized by the antibody. In one example, the first specific binding pair member is a receptor and the second specific binding pair member is a ligand.

As used herein, the terms "analyte" refer to any atom, chemical, molecule, compound, composition or aggregate of interest for detection and/or identification. Non-limiting examples of analytes include an amino acid, peptide, polypeptide, protein, glycoprotein, lipoprotein, nucleoside, nucleotide, oligonucleotide, nucleic acid, sugar, carbohydrate, oligosaccharide, polysaccharide, fatty acid, lipid, hormone, metabolite, cytokine, chemokine, receptor, neurotransmitter, antigen, allergen, antibody, substrate, metabolite, cofactor, inhibitor, drug, pharmaceutical, nutrient, prion, toxin, poison, explosive, pesticide, chemical warfare agent, biohazardous agent, radioisotope, vitamin, heterocyclic aromatic compound, carcinogen, mutagen, narcotic, amphetamine, barbiturate, hallucinogen, waste product and/or contaminant.

A "biological sample" includes, for example, urine, blood, plasma, serum, saliva, semen, stool, sputum, cerebral spinal fluid, tears, mucus, and the like. In certain aspects, the biological sample is from a mammalian subject, for example a human subject. The biological sample can be virtually any biological sample, as long as the sample contains or may contain a second specific binding pair member. For example, the sample can be suspected of containing a protein that has an epitope recognized by an antibody included as the first specific binding pair member. The biological sample can be a tissue sample which contains, for example, 1 to 10,000,000; 1000 to 10,000,000; or 1,000,000 to 10,000,000 somatic cells. The sample need not contain intact cells, as long as it contains sufficient quantity of a specific binding pair member for the methods provided. According to aspects of the methods provided herein, wherein the biological sample is from a mammalian subject, the biological or tissue sample can be from any tissue. For example, the tissue can be obtained by surgery, biopsy, swab, stool, or other collection method. In other aspects, the biological sample contains, or is suspected to contain, or at risk for containing, a pathogen, for example a virus or a bacterial pathogen.

As used herein, the term "nanocrystalline silicon" refers to silicon that comprises nanometer-scale silicon crystals, typically in the size range from 1 to 100 nanometers (nm). "Porous silicon," which contains nanosized silicon crystals, refers to silicon that has been etched or otherwise treated to form a porous structure.

As used herein, "operably coupled" means that there is a functional interaction between two or more units of an apparatus and/or system. For example, a Raman detector may be "operably coupled" to a computer if the computer can obtain, process, store and/or transmit data on Raman signals detected by the detector.

The term "binds specifically" or "specific binding activity," when used in reference to an antibody means that an interaction of the antibody and a particular epitope has a dissociation constant of at least about $1 \times 10^{-6}$, generally at least about $1 \times 10^{-7}$, usually at least about $1 \times 10^{-8}$, and particularly at least about $1 \times 10^{-9}$ or $1 \times 10^{-10}$ or less. As such, Fab, $F(ab')_2$, Fd and Fv fragments of an antibody that retain specific binding activity, are included within the definition of an antibody.

As used herein, the term "antibody" is used in its broadest sense to include polyclonal and monoclonal antibodies. The term antibody as used herein is meant to include intact molecules as well as fragments thereof, such as Fab and $F(ab')_2$, Fv and SCA fragments which are capable of binding an epitopic determinant.

(1) An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

(2) An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

(3) An $(Fab')_2$ fragment of an antibody can be obtained by treating a whole antibody molecule with the enzyme pepsin, without subsequent reduction. A $(Fab')_2$ fragment is a dimer of two Fab' fragments, held together by two disulfide bonds.

(4) An Fv fragment is defined as a genetically engineered fragment containing the variable region of a light chain and the variable region of a heavy chain expressed as two chains.

(5) A single chain antibody ("SCA") is a genetically engineered single chain molecule containing the variable region of a light chain and the variable region of a heavy chain, linked by a suitable, flexible polypeptide linker.

The term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., *Science* 246:1275-1281 (1989). These and other methods of making, for example, chimeric, humanized, CDR-grafted, single chain, and bifunctional antibodies are well known to those skilled in the art (Winter and Harris, *Immunol. Today* 14:243-246, 1993; Ward et al., *Nature* 341: 544-546, 1989; Harlow and Lane, *Antibodies: A laboratory manual* (Cold Spring Harbor Laboratory Press, 1988); Hilyard et al., *Protein Engineering: A practical approach* (IRL Press 1992); Borrabeck, *Antibody Engineering*, 2d ed. (Oxford University Press 1995.

Methods for raising polyclonal antibodies, for example, in a rabbit, goat, mouse or other mammal, are well known in the art (see, for example, Green et al., "Production of Polyclonal Antisera," in *Immunochemical Protocols* (Manson, ed., Humana Press 1992), pages 1-5; Coligan et al., "Production of Polyclonal Antisera in Rabbits, Rats, Mice and Hamsters," in *Curr. Protocols Immunol.* (1992), section 2.4.1). In addition, monoclonal antibodies can be obtained using methods that are well known and routine in the art (Harlow and Lane, supra, 1988).

As used in this invention, the term "epitope" refers to an antigenic determinant on an antigen, to which the paratope of an antibody binds. Antigenic determinants usually consist of chemically active surface groupings of molecules, such as amino acids or sugar side chains, and can have specific three-dimensional structural characteristics, as well as specific charge characteristics.

Examples of types of immunoassays of the invention include competitive and non-competitive immunoassays in either a direct or indirect format. Those of skill in the art will know, or can readily discern, other immunoassay formats without undue experimentation.

In performing a method of the present invention, "blocking agents" can be included in the incubation medium. "Blocking agents" are added to minimize non-specific binding to a surface and between molecules.

The term "receptor" is used to mean a protein, or fragment thereof, or group of associated proteins that selectively bind a specific substance called a ligand. Upon binding its ligand, the receptor triggers a specific response in a cell.

The term "polypeptide" is used broadly herein to mean two or more amino acids linked by a peptide bond. The term "fragment" or "proteolytic fragment" also is used herein to refer to a product that can be produced by a proteolytic reaction on a polypeptide, i.e., a peptide produced upon cleavage of a peptide bond in the polypeptide. A polypeptide of the invention contains at least about six amino acids, usually contains about ten amino acids, and can contain fifteen or more amino acids, particularly twenty or more amino acids. It should be recognized that the term "polypeptide" is not used herein to suggest a particular size or number of amino acids comprising the molecule, and that a peptide of the invention can contain up to several amino acid residues or more. A protein is a polypeptide that includes other chemical moieties in addition to amino acids, such as phosphate groups or carbohydrate moieties.

FIG. 1 illustrates an exemplary microfluidic channel 100 for performing methods provided herein that involves trapping a bead 150 with an attached single nucleic acid molecule 160 in a restriction barrier 140. The microfluidic channel 100 includes an immobilization structure, which in certain aspects of the invention is a restriction barrier 140. The restriction barrier 140 in this example includes a first angled wall 120 and a second angled wall 130 between which a single particle is captured. The first angled wall 120 and second angled wall 130 are spaced apart to allow a molecule such as a nucleotide molecule, a nucleic acid molecule and/or a protein such as an exonuclease, to flow between them. However, the first angled wall 120 and second angled wall 130 are spaced close enough to each other to retain the particle 150.

Accordingly, the first angled wall 120 and second angled wall 130 form a first opening 190 that is large enough to allow a single particle 150 to be captured by the restriction barrier 140, and a second opening 195 through which the particle 150 cannot pass. It will be understood that the height of the restriction barrier 140 is typically determined by the channel depth and that the dimensions of the restriction barrier 140 and its openings 190, 195 need to be commensurate with and are a function of the particle 150 dimensions. In certain example, the first opening 190 is between about 0.1 micron and about 100 microns in width and height, for example between about 1 micron and about 10 microns, or greater than 0.1, 0.25, 0.5, 1 microns, 2.5 microns, or 5 microns, and less than 1 millimeter, 500 microns, 250 microns, 100 microns, 50 microns, 25 microns, 10 microns. Opposite from the first opening 190 is a second opening 195 formed by the first angled wall 120 and the second angled wall 130 that is smaller than the diameter of the particle 105 so that the particle 150 is retained in the restriction barrier 140, yet large enough to allow molecules, such as nucleotides, nucleic acid molecules, or proteins to pass through. The second opening 195 is typically less than 10, 5, 4, 3, 2, or 1 micron, or less than 100, 10, 5, 4, 3, 2, or 1 nanometer, and typically at least 1, 2, 3, 4, 5, or 10 nanometers. The restriction barrier 140 is positioned within the microfluidic channel 100, such that when a particle 150 enters the microfluidic channel 100 it is captured in the restriction barrier 140 because fluid flow in the channel 100 moves the particle 150 from the large opening 190 towards the small opening 195. Typically, a particle 150 cannot exit a restriction barrier 140 along the direction of fluid flow after it enters the restriction barrier 140 provided that flow in the channel 100 continues to be directed into the restriction barrier 140.

The restriction barrier can include a plurality of walls, such as a plurality of angled walls. It will be understood that various configurations of walls can be used in the restriction barrier to restrain a particle. The restriction barrier can be configured in any way that provided that it restrains a particle that has an attached nucleic acid molecule that can be contacted with another molecule, such as an exonuclease. Furthermore, the restriction barrier is configured so that a nucleotide cleaved from a nucleic acid molecule attached to a captured particle, can is not trapped in the restriction barrier. Therefore, the restriction barrier typically has a first opening on the upstream portion of the barrier that is large enough for a nucleic acid molecule attached to a particle to enter the barrier, and a second opening on the downstream end of the barrier that is small enough to trap the nucleic acid molecule attached to the particle, inside the barrier. For example, the restriction barrier can be L-shaped using rectangular brackets, or funnel shaped, allowing a nucleic acid molecule and/or a protein to flow through, while still retaining the particle. Other possibilities for the restriction barriers include using polymer filters or porous membranes such as cellulose acetate and alumina membranes with pore sizes smaller than the particle diameter.

Where the restriction barrier includes a first angled wall and a second angled wall, many different angles can be used for the walls provided that the restraining barrier can restrain a particle yet provide access to a nucleic acid molecule attached to the particle. For example, the first angled wall and the second angled wall can form an angle of between 5° and 90°, or between about 10° and 75°. The first and second angled walls can be identical lengths or they can be different lengths. In one aspect, one angled wall is longer and functions as a ramp to guide a particle into the restriction barrier. The first and second walls are typically between 1 micron and 10 millimeters in length and between 10 nanometers and 1 micron in width.

Molecular interactions or attractive forces between the angled walls and the bead or nucleic acid can be used to restrain and/or position the bead, or to assist in this restraint or positioning. In other words, the restraint of the particle need not be physical but also can include chemical attachment or other forces. For example, magnetic forces can be employed. Alternatively, the angled walls can include a first specific binding pair member and the beads or nucleic acid molecule can include a second specific binding pair member. For example, an angled wall can include one or more avidin moieties attached to its surface and a particle can include one or more biotin moieties. By the binding of a first specific binding pair member to a second specific binding pair member, the particle is further restrained within the restriction barrier. Furthermore, functionalizing the material of the walls can be used to reduce adhesion of particle to the wall.

The restriction barrier walls can be made from a variety of materials. For example, the walls can be molded in the microchannel and made of an identical composition as the microchannels. Methods for micromolding microfluidic devices are provided herein Any crosslinkable or polymerizable fluid could be used to construct the angled walls of the restraining barrier. For example, hydrogel can be used to construct the barrier. Fabrication of the barriers is done by essentially filling the channels first with the polymerizable fluid and then exposing it to a polymerizing agent such as UV radiation, through a mask and then flushing the unpolymerized fluid leaving the polymerized restriction barrier within the microchannel. The mask determines the shape and dimensions of the barrier.

A particle used in the present invention methods can be a wide range of sizes, shapes, and materials, provided that a nucleic acid can be attached to the surface of the particle, the particle can be captured, transported, and released by optical tweezers, and movement of the particle can be restrained in a restriction barrier. For example, the particles can be surface-functionalized microsphere beads. Suitable beads of varying sizes are commercially available (Bangs Laboratories, Inc., Fishers, Ind.). The microsphere beads typically have a diameter of between about 0.1 microns ($\mu$) and about 20$\mu$, for example between about 0.5$\mu$ and about 10$\mu$, and as a more specific example between about 1$\mu$ and about 5$\mu$. The microsphere beads can be made of materials such as polystyrene, glass, polysaccharides such as agarose, and latexes such as styrene butadiene. In certain aspects, the particle can be in the form of magnetic or non-magnetic beads or other discrete structural units.

Various methods can be used to attach a single nucleic acid molecule to a particle. As discussed in more detail below, methods are known for immobilizing a nucleic acid to a solid support, such as a particle. To attach a single nucleic acid molecule to a particle using virtually any known method for immobilization, a sample containing the nucleic acid molecule can be diluted prior to coupling it to a particle. At an appropriate dilution, each particle will have a statistical probability of binding zero or one nucleic acid molecule. Particles with one attached nucleic acid molecule can be identified using, for example, fluorescent dyes and flow cytometer sorting or magnetic sorting.

In another embodiment, a single molecule is attached to a particle by contacting nucleic acid molecules that are immobilized in a channel surface with particles. In illustrative examples, the nucleic acid molecules are spaced far enough apart on the channel surface so that a particle can only bind to one nucleic acid molecule (See U.S. patent application Ser. No. 10/748,802, filed Dec. 30, 2003, entitled "METHOD AND DEVICE FOR ISOLATING SINGLE POLYMERIC MOLECULES," inventors Narayanan Sundararajan and Xing Su, and U.S. patent application Ser. No. 10/781,238, filed Feb. 18, 2004, entitled "METHOD AND DEVICE FOR ISOLATING AND POSITIONING SINGLE MOLECULES," inventors Narayanan Sundararajan, Xing Su, and Tae-Woong Koo). Typically, the particle is attached to the nucleic acid molecule as the result of binding of a first specific binding partner on the particle to a second specific binding partner on the nucleic acid molecule. For example, the particle can include avidin moieties on its surface and the nucleic acid molecule can include biotin moieties.

More specifically, in certain examples nucleic acid molecules can be modified/labeled on one end and immobilized to specific binding positions on a substrate surface of a channel, such that the shortest distance between two adjacent binding positions is at least about two times the length of particles to which the nucleic acids are to be attached. The specific binding positions, which typically are formed by immobilizing a first specific binding pair member on the channel surface, can be downstream from the detection unit and downstream from a flow of nucleic acid molecules. Nucleic acid molecules include a second specific binding pair member that binds to the first specific bind pair members on the channel surface.

A nucleic acid labeled with a specific binding pair member preferably is bound to the substrate surface via the non-labeled end only. Unbound nucleic acid molecules (i.e., nucleic acid molecules that have not attached to a binding position) are typically washed off of the substrate surface after the immobilization of the nucleic acid molecules. Immobilized nucleic acid molecules are subsequently contacted with particles that have specific binding members on their surface that bind to a specific binding pair member attached to the nucleic acid molecule. Free particles can be carried away from the channel surface by the flow within the channel. After the particles bind to the nucleic acid molecules they are released from the substrate by breaking the association of the nucleic acid molecule with the specific binding position on the substrate surface. Optical tweezers are then used to capture a single particle with an attached single nucleic acid molecule and transport the single particle upstream of a restriction barrier. As indicated above, the nucleic acid molecules are spaced far enough apart on the surface to assure that a particle cannot bind to more than a single nucleic acid molecule.

According to another aspect of the invention, a single nucleic acid molecule associated with a particle can be isolated by introducing particles with varying numbers of attached nucleic acid molecules into an applied electric field, and isolating particles having only one attached nucleic acid molecule from the remainder of particles. Separation of the particles based on the number of attached nucleic acid molecules occurs because the nucleic acid molecule changes the charge of the particle, therefore also affecting its mobility in an applied electrical field.

In certain aspects, the immobilization structure for restraining movement of the particle is a surface of a flow channel, or a substrate attached to a surface of the flow channel, upstream from the SERS detection unit. Various molecular interactions or forces can be used to restrain a particle on a surface provided that attachment of the particle to the immobilization structure is strong enough to withstand the flow of liquid in the channel. For example, magnetic forces can be used. Furthermore, the immobilization structure can include a cross-linking agent, for immobilizing the particle. Optical tweezers are used to transport and release the particle within the channel so that it can be carried by the flow of the channel into contact with the immobilization structure.

When the methods provided are used to determine a nucleotide sequence of a nucleic acid molecule, the identity and sequence of between 1 nucleotide and all of the nucleotides of the nucleic acid molecule can be determined. For example, a nucleotide sequence of less than 2, 3, 4, 5, 10, 15, 20, 25, 50, 100, 150, 200, 250, 500, 1000, 1500, or 2000 nucleotides can be determined.

FIG. 2 illustrates a specific example of a system for performing a method provided that involves optical tweezers 210 and a restriction barrier 140. The microfluidic system 200 includes a first channel 100; a second channel 220 in fluid communication with the first channel 100, wherein the first channel 100 delivers particles 150 into the first channel 100; a third channel 230 in fluid communication with the first channel 100, wherein the third channel 230 delivers nucleic acid molecules 160 into the first channel 100; optical tweezers 210 to capture, transport, and release a single particle 150; and a SERS detection unit in optical communication with the first channel at a detection area 240 downstream of the restriction barrier.

Using this system, which is typically a MEMS system, particles 150 are transported into the first channel 100 by the flow of the second channel 220 where they contact nucleic acid molecules 160 delivered from the third channel 230, downstream of the junction of the second channel 220 and third channel 230 with the first channel 100. A single nucleic acid molecule 160 is attached to the surface of the particle 150. The optical tweezers 210 then capture a single particle 150 with an attached nucleic acid molecule 160 downstream form the restriction barrier 140 and downstream of a junction of the first channel 100 and the second channel 220 and/or third channel 230, transport the particle 150 upstream of a restriction barrier 140, and release the particle 150. The particle 150 is then moved by the flow of the first channel 100 into the restriction barrier 140 inside which its movement is restrained. Next, an exonuclease or other molecular destruction reagent in the first channel 100 contacts the nucleic acid molecule 160 and cleaves a terminal nucleotide. The cleaved nucleotide travels downstream in the first channel 100 and is detected by the SERS detection unit in a detection area 240. The detection area 240 is an area in the first channel 100, or a channel connected thereto, downstream of the restriction barrier 140. The SERS detection unit is in optical communication with the detection area 240.

A reaction area is an area within the first channel where a nucleic acid molecule is made available to an exonuclease or other destruction agent. The reaction area is located upstream of the SERS detection unit. Typically, the reaction area contacts and/or surrounds the immobilization substrate, for example the restriction barrier. In certain aspects, the reaction area is located upstream of the junction of a first channel, which carries particles, and a second channel, which carries nucleic acid molecules.

In methods, systems, and apparatus provided, optical tweezers are positioned in a first channel to capture a single particle downstream from a restriction barrier in the channel, transport the particle upstream of the restriction area, and release the particle so that it can be captured in the restriction barrier.

"Optical tweezers" are tightly focused beams of laser light that can be used to trap and remotely manipulate polarizable objects (See e.g., U.S. Pat. Nos. 5,620,857; 5,100,627; and 4,893,886). Originally proposed for the trapping of atoms, such devices are also capable of trapping macroscopic, polarizable objects such as latex and glass spheres in the micron size range as well as biological material such as viruses, bacteria, yeast and protozoa, ranging in size from 20 nm to 100 microns. Not wanting to be limited by a particular theory, the basic principle behind optical tweezers is the gradient force of light which manifests itself when a transparent material with a refractive index greater than the surrounding medium is placed in a light intensity gradient. As light passes through the polarizable object, it induces fluctuating dipoles in the material. These dipoles interact with the electromagnetic field gradient, resulting in a force directed towards the brighter region of the light. Hence the object is pulled into the focus of the laser beam which is the local maximum of the light rigid.

Single-beam gradient force traps have been demonstrated for neutral atoms and dielectric particles. Generally, the single-beam gradient force trap includes a strongly focused laser beam having an approximately Gaussian transverse intensity profile. In these traps, radiation pressure scattering and gradient force components are combined to give a point of stable equilibrium located close to the focus of the laser beam. Scattering force is proportional to optical intensity and acts in the direction of the incident laser light. Gradient force is proportional to the optical intensity and points in the direction of the intensity gradient.

Particles in a single-beam gradient force trap are confined transverse to the laser beam axis by a radial component of the gradient force. Stabilizing the particle along the axis direction of the trap is achieved by strongly focusing the laser beam to have the axial component of gradient force dominate the scattering force in the trap region.

The wavelengths of the laser light source of the optical trap can be in the visible range, but are typically in the infrared frequencies. One example of an optical trap laser is a standard laser emitting a coherent light beam substantially in the infrared range of wavelengths, for example, 0.8 μm to 1.8 μm. Optical trapping can also be conducted using visible wavelengths for example at 532 nm and 1064 nm, or using an argon ion laser (488 nm, 514 nm) or a HeNe laser (632 nm). The light beam from the laser impinges upon a combination of optics elements for focusing the light beam with a sufficient degree of convergence to form a single-beam gradient force optical trap for confining particles at a desired position. The combination of optics elements includes an adjustably mounted diverging lens and a high convergence lens.

In another series of related embodiments, referred to herein as "the hydrodynamically focusing methods," methods are provided to control position-specific reactions using microfluidic alignment and hydrodynamic focusing. These methods overcome the current need for methods that are simpler, more efficient, and less costly. "Hydrodynamic focusing" is a reduction in cross-sectional dimension or area of a first flow along a flow axis by contacting the first flow with two side flows within a channel, wherein the direction of the two side flows is the same as the direction of the first flow. The side flows are termed sheath flows and they "squeeze" the first flow due to conservation of mass. The "side" flows need not necessarily be in the lateral direction but can also be in the vertical direction.

Suitable sources for introducing fluids into microfluidic channels include, but are not limited to, pumps, such as syringes or micro-fluidic pumps, and channels or chambers having sufficient pressure to promote flow. Electrokinetic and electroosmotic flows driven by voltages can also be used. Furthermore, electrodes can be fabricated into the outlets to focus the stream as well. The fluids may be introduced as either steady flows or intermittent flows (for example discrete pulses). The flow rates of the fluids can be the same or different.

A hydrodynamic focusing system can receive fluids from the sources. The hydrodynamic focusing system includes a first micro-fluidic inlet channel coupled with a first fluid source at a first end thereof, and typically a second micro-fluidic inlet channel coupled with a second fluid source at a first end thereof, and a third micro-fluidic inlet channel coupled with a third fluid source at a first end thereof. For example, the first fluid can be a hydrodynamically-focused delivery flow, wherein the second and third fluids can be protective flows. Other configurations of flows is possible such as the 3-D focusing or using chimney structures where the sample stream enters the bottom through the hole to the main microfluidic channel.

The channels represent micro-sized fluid passages that can have a cross-sectional dimension, such as a channel width, height, or diameter, of less than approximately 1000 µm, 500 µm, or 100 µm. These minute dimensions promote laminar flow, which is conducive to hydrodynamic focusing. There is no known minimum or maximum length for the channels, although often the lengths are in a range between at least several times the channels widths and several centimeters. The first inlet channel approaches the second inlet channel from a first side thereof, at an angle, and the third inlet channel, when present, typically approaches the second inlet channel from a second, opposite, side thereof, at an angle.

A wide variety of focusing fluids can be employed. Examples include but are not limited to water, aqueous solutions, organic solvents, organic solutions, and mixtures thereof. The use of a relatively viscous fluid may be appropriate to promote laminar flow and reduce diffusion. Generally the fluids in the channels should be compatible, relatively inert, and should not solidify.

The focusing fluids are received from the inlet channels into a focusing manifold of the hydrodynamic focusing system. The focusing manifold is coupled with second ends of each of the inlet channels. The focusing manifold represents a junction where the second ends of the inlet channels come together and join. The fluids may be discharged from the channels into the focusing manifold where they contact each other and hydrodynamic focusing is initiated. Hydrodynamic focusing generally involves contacting a plurality of flows in the focusing manifold and focusing or otherwise reducing a cross-sectional dimension or area of one or more flows along a flow axis in the confines of the hydrodynamic focusing system. In a representative example of hydrodynamic focusing, a delivery fluid and a protective fluid are contacted in the focusing manifold. In the laminar flow regime, which generally occurs in micro-fluidic channels and chambers, the fluids do not mix significantly, but tend to come into alignment as side-by-side co-axial flows. The laminar flow regime may be characterized by a Reynolds number that is less than approximately 2300, 1000, 100, 10, 1, 0.1, or 0.01. A small amount of diffusion at interfaces between the fluids may be tolerated. At contact, the fluids may exert hydrodynamic forces or pressures on one another. Within the confines of the hydrodynamic focusing system, for example at the entrance to the outlet channel, the forces or pressures may focus or otherwise reduce cross-sectional dimensions or areas of the flows along a flow axis.

When fluids delivered through the inlet channels have similar hydrodynamic forces, for example similar flow rates and pressures, the regions occupied by the fluids in the outlet channel tend to be similar. As shown in FIG. 5, each of the fluid flows occupy approximately one-third proportion of the flow cross section of the outlet channel, although this is not required. Optionally, different hydrodynamic forces may be employed to allow one fluid to occupy a larger or smaller region than another fluid. Increasing the flow rate or pressure of one or more fluids generally increases the amount of focusing and decreasing the flow rate or pressure of one or more fluids generally decreases the amount of focusing.

The amount of focusing also depends upon, and tends to vary inversely with, the cross-sectional area of the outlet channel available for flow. The outlet channel can be dimensioned about the same as any one of the inlet channels, although this is not required. Increasing the cross-sectional area can decrease the amount of focusing and decreasing the cross-sectional area can increase the amount of focusing. By adjusting the dimensions of the outlet channel, and the flow rates and pressures of the fluids, the amount of focusing may be varied from a small amount to a large amount.

Existing technologies attempt to direct a reactant to a desired position by specific binding, such as by DNA hybridization which requires specific sequences and special targets such as single-stranded DNA. Furthermore, methods have been developed for directing reactants to a subcellular position with laminar flow of a width of about 10 µm (Takayama et al, Nature, 2001, 411, p 1016). This technology uses hydrodynamic focusing to deliver a reagent to one side of a cell that includes about a 10 µm section of the cell. However, this technology does not allow the precision of focusing necessary for directing a reactant to a specific region of another molecule.

Synchronization of multiple-molecule polymer reactions is another unsolved problem. For example in exonuclease DNA sequencing, also called direction DNA sequencing, individual DNA molecules bind to an exonuclease with different rates due to their un-controlled conformation. The difference in initial binding rate is amplified during step-wise nucleotides removal, as the nucleotide removal is faster than the initial binding (Wuite et al, Nature, 2000, 404, p 103-106). This rate difference makes it very difficult to detect the removed nucleotides. For example, among 100 copies of a nucleic acid molecule having a sequence 5'-ATCGATAC-GATCG, (SEQ ID NO: 1) at a particular timepoint during an exonuclease reaction, some copies of the nucleic acid molecule may be releasing the 3' terminal guanidine residue, while others may be releasing the penultimate 3' terminal cytidine residue.

To synchronize nucleic acid sequencing reactions, the use of thermostable and photoactivating enzymes has been disclosed (See e.g., U.S. Pat. No. 5,674,743). However, thermostable or photoactivating enzymes with exonuclease activity do not exist now. Furthermore, even if such an enzyme is engineered, it will be very difficult to limit the enzyme's catalytic activity to a certain temperature range, or to a photoactivated state.

Another presently unsolved problem is that site-specific reactions on molecules often give lower yield due to side reactions. For example, in solid-phase oligo-nucleotide synthesis, the per-step yield for short products (i.e. <50 nucleotides) can be as high as 99%. However, the yield drops dramatically as the length increases, for example to below 90% at lengths of over 100 nucleotides. Furthermore, sideproducts accumulate fast from reactions in regions within the oligonucleotide chain, rather than at the ends. When the length of a synthesized nucleic acid molecule reaches 100 nucleotides, over 80% of the reaction products are found to be side products due at least in part to the fact that some ends of the nucleic acid molecule are buried in the polymer chain. This limits the synthesis of long oligonucleotides and hence their availability for various applications.

Provided herein are methods that overcome these shortcomings of current methods, by using fluidic alignment to lock the conformation and orientation of a reactant before confining a reaction to a very small area (e.g., linear scale ~0.1 um for sequencing) by hydrodynamic focusing. This results in simpler, more synchronized methods that provide higher yield and higher purity products. Better synchronization is achieved because a molecule can be delivered precisely to a desired reactive region (i.e. a target region) of another molecule, and this target region can be moved over time as a reaction proceeds. Higher yield is the result of the fact that microfluidic alignment exposes an end of a reactant when an end reaction is desired (e.g., exonuclease reaction, carbon nanotube end modification), thereby enabling the reagent to find the end easily. Higher purity is the result of the fact that by focusing the reactant flow, side reactions on other parts of a molecule can be minimized. Furthermore, the invention methods are simpler than existing methods because fluidic control allows continuous synthesis, rather than the multiple steps required in most current methods.

Methods provided herein control position-specific reactions using microfluidic alignment and hydrodynamic focusing. In order to confine reactions to the desired position of molecules such as DNA, proteins, and carbon nanotubes, the entire molecule or one end of the molecule is immobilized on a surface. Microfluidic alignment followed by drying is then used to "lock" the molecules in a specific conformation. Once the molecules have been immobilized on the surface in the desired location and conformation, microfluidic hydrodynamic focusing can be utilized to direct a reagent specifically to a desired position of the molecule. Furthermore, the hydrodynamically focusing methods are useful to synchronize nucleic acid sequencing reactions.

Not wanting to be limited by a particular theory, it is believed that the invention method is based in part on the following facts: (a) fluidic alignments of nucleic acids and semiconductor nanowires have been reported in the literature; (b) both double-stranded and single-stranded nucleic acids have been aligned; (c) two and three-dimensional microfluidic focusing have been developed (See e.g., U.S. patent application Ser. No. 10/609,227, filed Jun. 26, 2003, inventors Narayan Sundararajan and Andrew Berlin); (d) Submicron fluidic focusing on a silicon chip has been reported (Knight et al, "Hydrodynamic Focusing on silicon chip", Phy. Rev. lett., 1998, 80, p 3863-3866.); (e) fluidic-controlled reaction in select regions of a cell has been demonstrated (i.e. "Laminar flows—sub cellular positioning of small molecules", Takayama et al, Nature, 2001, 411, p 1016); and (f) fluidic alignment of DNA on orthogonal directions has been demonstrated (Wooley et al, Nano Lett., 2001, 1, p 345-348; illustrating that once the DNA is aligned and dried on surface, its conformation is locked even if it is exposed to a $2^{nd}$ fluid flow that is to another direction).

In addition to the above facts, the methods are based, in part, on the reactivity of surface-bonded DNA and protein molecules has been demonstrated by various reactions that are performed on DNA and protein chips (e.g. hybridizations and polymerizations). Furthermore, exonuclease reactions on oligonucleotides that are immobilized on surface have been successfully performed. These studies indicate that enzymes (or reactants) react with immobilized nucleic acids, proteins, or other molecules such as carbon nanotubes, even when their conformations are locked.

Accordingly, provided herein is a method for contacting a first molecule with a second molecule within a microfluidic device, that includes delivering at least one hydrodynamically focused flow through the microfluidic device, wherein the hydrodynamically focused flow brings the second molecule into contact with the first molecule only at a target region of the first molecule.

Figure 3A:
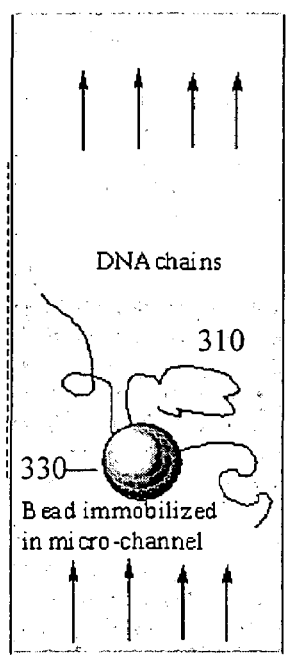
FIGS. 3A-3C illustrates an embodiment wherein fluidic alignment is used in a nucleic acid molecule synthesis reaction.
Figure 3B:
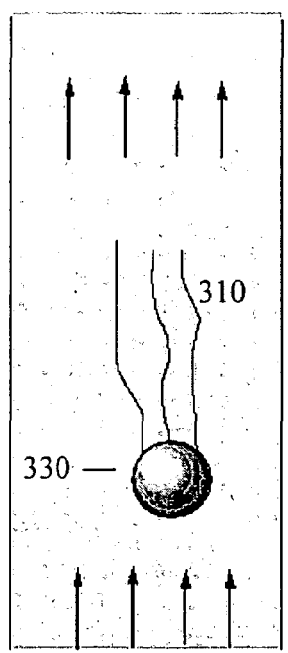
Figure 3C:
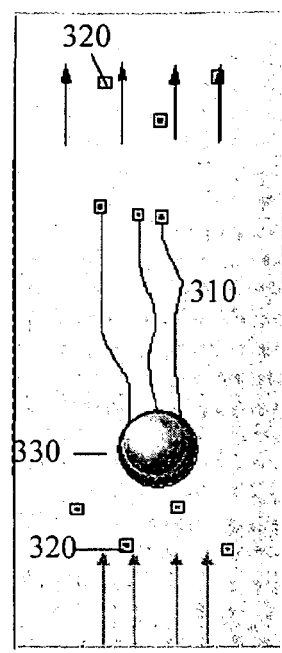

The methods provided are useful, for example, for improving the yield of an oligonucleotide synthesis reaction, as illustrated in FIG. 3. Accordingly, molecules contacted in methods disclosed herein include reactants typically used in nucleic acid synthesis, such as the well known phosphoramidite method. Typically, the first molecule is a nucleotide or a growing nascent nucleic acid molecule 310 to which monomers 320, phosphoramidite nucleotides, (i.e. the second molecule) are incorporated. A nascent nucleic acid molecule 310 that is attached to a solid support 330 can be aligned using fluidic alignment (FIG. 3A). Fluidic alignment exposes the ends of the nucleic acid molecules 310 (FIG. 3B). As a result of the fluidic alignment, monomers (i.e. phosphoramidite nucleotides 320) have better access to the end of the nucleic acid 310 (FIG. 3C), which is expected to result in better yield.

As is well known, in the phosphoramidite method, a series of deprotection, coupling, capping, and oxidation steps are repeated until a single stranded nucleic acid molecule of interest is synthesized. The nucleic acid molecule is formed 3' to 5', the direction opposite that of nucleic acid synthesis within cells. The first step typically utilizes a substrate that has a protected form of the terminal (3') monomer chemically bound to its matrix. The nascent oligonucleotide chain will stay attached to this substrate as each activated monomer, one by one, is linked to its 3' neighbor. The substrate is contained in a reaction vessel, such as a microchannel, where it reacts with reagents released into the reaction chamber at specific times throughout a synthesis cycle. Protected monomers are typically deoxyribonucleoside 3-phosphoramidites containing dimethoxytrityl (DMT) blocking groups on the 5'-oxygen atoms. These monomers are activated by treatment with a weak acid prior to chain elongation. In methods of the present invention, either the entire nucleic acid molecule synthesis reaction, or parts of this reaction, are performed while a fluid flow aligns a nascent nucleic acid molecule 310.

Referring to FIG. 4, hydrodynamic focusing methods can be used in nucleic acid exonuclease sequencing reactions. The method can be performed, for example, in a microfluidic device, such as a MEMS device, that includes valves 420 for controlling the flow between microchannels 410. Typically, a nucleic acid molecule 310 (i.e. a first molecule) is immobilized on a solid support 330. Furthermore, the nucleic acid molecule 310 is aligned before it is contacted with an exonuclease (i.e. a second molecule) (not shown). Valves 1 and 3 are opened to allow for in situ nucleic acid synthesis, such as disclosed in FIG. 3, or immobilization of a nucleic acid molecule 310 on a solid support 330. For example, as shown in FIG. 4B, nucleic acid molecules can be captured on the solid support by flowing a solution that contains the nucleic acid molecules through microchannels so that the nucleic acid molecules contact the solid support 330. Various methods for immobilizing a nucleic acid molecule 310 to a solid support 330 are known.

The captured nucleic acid molecules 310 are then aligned using fluid flow (represented by arrows) and surface tension (FIG. 4C). If a nucleic acid molecule 310 is synthesized in situ within the microfluidic channel, the nucleic acid molecule 310 is aligned during synthesis, as disclosed with respect to FIG. 3. Alignment of the nucleic acid molecule 310, in addition to facilitating nucleic acid synthesis, facilitates accurate positioning of at least one hydrodynamically focused flow at a target region of the nucleic acid molecule 310. The target region, for example, can be the end of the nucleic acid molecule 310. The microchannel is then dried to "freeze" or "lock" the nucleic acid molecule 310 in the desired aligned confirmation as illustrated in FIG. 4D. Valves 1 and 3 are closed, and valves 2 and 4 are opened to dry the microchannel. Next, exonuclease molecules, or other deconstruction reagents, in a buffer are delivered to a 3' terminus of the nucleic acid molecule 310 in a delivery flow using two-dimensional hydrodynamic fluidic focusing (FIG. 4E). A delivery flow is a flow that transports a suspended molecule in a microchannel to a site of a reaction. In this example, the delivery flow transports the deconstruction reagent to the target region of the nucleic acid molecule. As disclosed herein, for reactions involving terminal nucleotides of a nucleic acid molecule 310, the hydronyamic flow can be focused, for example, to a width of about 0.05 to about 0.15 microns (linear scale), to include a 3' terminus of the nucleic acid molecule. Upon exposure of a terminus of the nucleic acid molecule 310 to the exonuclease molecules, terminal nucleotides 430 are cleaved by the exonuclease molecules and carried downstream for analysis (FIG. 4F). Analysis is typically SERS analysis performed using a SERS detection unit (not shown). Typically, only the target region of the nucleic acid molecules 310 are digested, although it is possible that a much lower rate of digestion can occur at non-target regions of the nucleic acid molecule 310 if a small number of exonuclease molecules escape from the hydrodynamically focused flow.

Immobilized molecules such as nucleic acids, nanotubes, or nucleic-acid wrapped nanotubes can be aligned using any of a number of known techniques. An exemplary method for aligning nucleic acids on a substrate is known as molecular combing. (See, e.g., Bensimon et al., Phys. Rev. Lett. 74:4754-57, 1995; Michalet et al., Science 277:1518-23, 1997; U.S. Pat. Nos. 5,840,862; 6,054,327; 6,225,055; 6,248, 537; 6,265,153; 6,303,296 and 6,344,319.) In this technique, nucleic acids or other hydrophilic polymers are attached at one or both ends to a substrate, such as a silicon chip. The substrate and attached nucleic acids are immersed in a solution, such as an aqueous buffer, and slowly withdrawn from the solution. The movement of the air-water-substrate interface serves to align the attached nucleic acids, parallel to the direction of movement of the meniscus.

The method of polymer alignment used is not limiting and any known method, including but not limited to use of optical tweezers, DC and/or AC electrical fields, microfluidic flow, and/or magnetic fields is contemplated. In another non-limiting example, nucleic acids or other charged polymers can be aligned on a substrate by free flow electrophoresis (e.g., Adjari and Prost, Proc. Natl. Acad. Sci. U.S.A. 88:4468-71, 1991). The surface can comprise alternating bands of conductive and non-conductive materials that function as electrodes, or other types of microelectrodes can be used. In the presence of an alternating current electrical field, polymers including charged residues, such as the phosphate groups on nucleic acids, will align with the field (Adjari and Prost, 1991). The method is not limited to nucleic acids and can be applied to proteins or other polymers containing charged groups. Where the charge on the polymer is not fixed, the net charge can be manipulated, for example by changing the pH of the solution. Fluidic alignment of various types of polymer molecules (i.e. molecular wires or concatenated molecular chains), has been demonstrated (Bensimon et al., *Science*, 265: 1096-98 (1994) (double stranded DNA); Lieber et al., *Science*, 291:630 (2001)(semiconductor nanowires); Lienemann et al., *Nano-letters*, 1:345 (2001) (single-stranded DNA)).

In certain specific examples, the dynamic focusing conditions are changed over time to move the target region to focus on the retracting terminus of the nucleic acid molecule 310 as terminal nucleotides 430 are cleaved by the exonuclease. This is expected to result in improved synchronization of the cleavage reaction because the exonuclease is delivered precisely to a desired reactive region (i.e. target region) of the nucleic acid molecule 310 as the terminus of the nucleic acid molecule 310 shortens. For example, the reaction can be performed in phases with a different target region for each phase.

The target region of a dynamically focused flow can be changed by changing the reaction conditions. Reaction conditions can be changed, for example, by changing the pressure of the side streams. Accordingly, side stream pressure can be reduced in a second phase, to enlarge the width of the hydrodynamically focused flow (FIG. 4G). This results in cleavage of nucleotides in a second target region. For example, if the fluid flow is widened by approximately 0.05 microns, during the second phase an additional 150 bases will be sequentially cleaved from the 3' terminus of the nucleic acid molecule 310. After the second phase reaction stops, additional phases can be performed using increasing hydrodynamically focused flow widths (FIG. 4H), to cleave additional nucleotides. In order to minimize binding of reactants to walls of the microfluidic channels, the side streams can be protective streams.

As indicated above, the width and/or diameter of the hydrodynamic flow can be controlled by changing pressure of side streams that are used to focus the hydrodynamically focused delivery stream. Furthermore, the target area can be changed, for example, by increasing the pressure of one side flow, and reducing the pressure of another side flow, by moving the delivery of the flow within the channel, or by changing the viscosity of one o more of the flows.

In another aspect, electrodes are used to change the focusing characteristics and position as well (Wang et al., "Electrical Molecular Focusing For Laser Induced Fluorescence Based Single DNA Detection", Technical Digest of the 15th IEEE International Conference on MEMS (ISBN-0-7803-7187-9) (MEMS 2002)). The electrodes can be arranged to provide 3-D electric molecular focusing. A middle electrode can be applied with positive potential and two side electrodes can be grounded. Negatively charged biomolecules, such as DNA molecules and most proteins, are concentrated to the middle electrode. One advantage of electrode focusing is that it does not require continuous flow.

The width or diameter of the hydrodynamic focused flow in the methods provided is typically less than 10 microns, and in certain aspects is less than 5, 4, 3, 2, 1, 0.5, 0.4, 0.3, and 0.2 microns (linear scale), but at least 0.05 microns (linear scale). For certain aspects of the invention for focusing a flow on a nucleic acid molecule, such as nucleic acid synthesis reactions and exonuclease sequencing reactions, a flow is focused to between about 0.5 and about 0.05 microns (linear scale), between about 0.2 and about 0.1 microns (linear scale), or to about 0.1 microns (linear scale). Finer focusing can likely be obtained using electrode focusing.

In another aspect, methods provided herein are useful for labeling nanotubes. Accordingly, in these aspects the first molecule is a nanotube and the second molecule is a label. For these aspects, the hydrodynamically focused flow is targeted at an end of the nanotube. Therefore, the methods are useful for directing labels to specific target regions of nanotubes. The width of the focused flow is typically between about 0.05 and 0.2 microns. The labels can include virtually any label known to be associated with nanotubes, including the disclosed Raman labels. These aspects are useful for example, to label the ends of nanotubes or to functionalize nanotubes with DNA. Furthermore, both a functionalization reaction and attachment can be performed using the same apparatus. These aspects can also be used for cutting nanotubes at particular lengths after alignment and immobilization.

Nanotubes can be made in a variety of shapes and sizes. (See, e.g., Freitag et al., Phys. Rev. B 62:R2307-R2310, 2000; Clauss et al., Europhys. Lett. 47:601-607, 1999; Clauss et al., Phys. Rev. B. 58:R4266-4269, 1998; Odom et al., Ann. N.Y. Acad. Sci. 960:203-215, 2002). Nanotubes can have tube lengths of about 10 to 200 nm and a diameter of about 1.2 to 1.4 nm. The length or diameter of the nanotubes to be used in methods of the present invention is not limited and nanotubes of virtually any length or diameter are contemplated. However, in a labeling method wherein nanotubes are aligned and then labeled, nanotubes that are labeled typically have a similar length (e.g. within 25 nm of each other) so that a hydrodynamically focusing flow can contact the ends of all the nanotubes.

Nanotubes can be prepared by known methods or obtained from commercial sources, for example, CarboLex (Lexington, Ky.), NanoLab (Watertown, Mass.), Materials and Electrochemical Research (Tucson, Ariz.) or Carbon Nano Technologies Inc. (Houston, Tex.). Some processing of either synthesized or purchased nanotubes may be appropriate before use. Processing may include purification of nanotubes from other contaminants, separation of nanotubes of mixed diameter and/or length into nanotubes of discrete diameter and length, and removal of nanotube end caps.

Carbon nanotubes can be produced by a variety of techniques known in the art, including but not limited to carbon-arc discharge, chemical vapor deposition via catalytic pyrolysis of hydrocarbons, plasma assisted chemical vapor deposition, laser ablation of a catalytic metal-containing graphite target, or condensed-phase electrolysis. (See, e.g., U.S. Pat. Nos. 6,258,401, 6,283,812 and 6,297,592.) In some embodiments, nanotubes may be size sorted by mass spectrometry (See, Parker et al., J. Am. Chem. Soc. 113:7499-7503, 1991) before they are attached to a surface, aligned, and end labeled. Alternatively, nanotubes may be sorted using an AFM (atomic force microscope) or STM (scanning tunneling microscope) to precisely measure the geometry of individual nanotubes before labeling them. Other methods of size fractionation known in the art, such as gas chromatography, time of flight mass spectrometry, ultrafiltration or equivalent techniques are contemplated. Once sorted, the carbon nanotubes can be attached to a label.

In another embodiment, provided herein are methods to prevent non-specific binding of proteins and other biomolecules or particles on surfaces of microfluidic channels. The methods involve using one or more laminar flows (protective flows) in a microfluidic channel to protect one or more surfaces of the channel from non-specific binding of biomolecules or particles. The protective flows are adjacent to the surfaces where non-specific binding is not desired, such as a surface of a microfluidic channel, and have thicknesses that can be controlled. Typically, the first molecule is immobilized on a solid support before it is The protective flow can contain reduced levels of, or be free of active biomolecules or particles that could bind to the specific surfaces. Furthermore, the protective flow can include non-specific blocking agents, such as bovine serum albumin or salmon sperm DNA, as are known in the art.

Figure 5A:
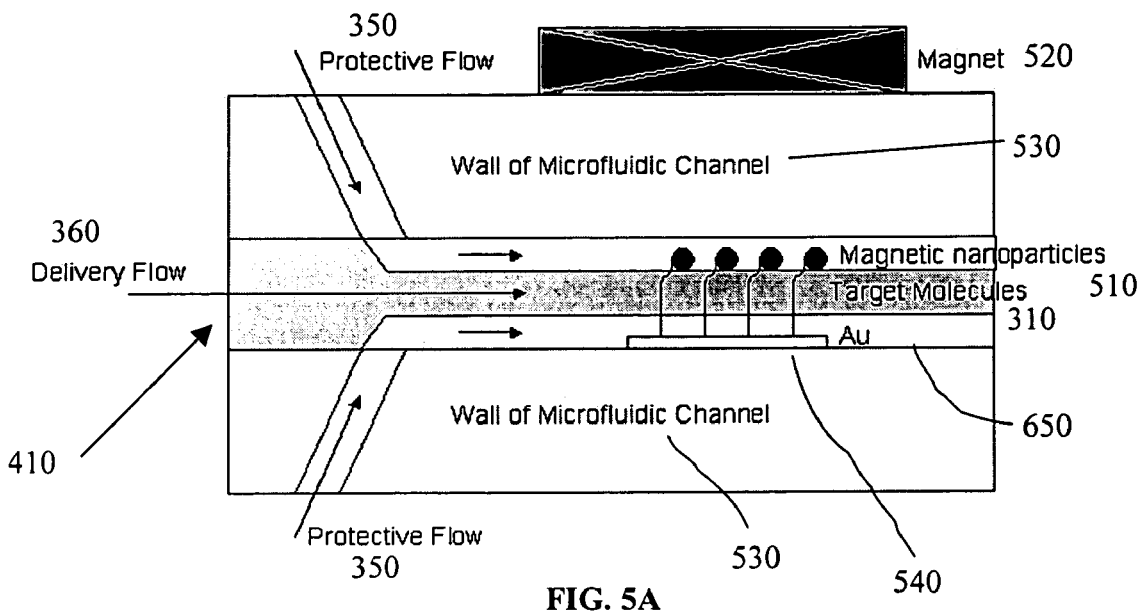
FIGS. 5A and 5B illustrate a microfluidic system that includes protective flows 350 and a delivery flow 360. A target molecule 310 is aligned using a magnetic force (FIG. 5A) or an electric field (FIG. 5B), before a second molecule is delivered to a target region of the target molecule 310 by a delivery flow 360.
Figure 5B:
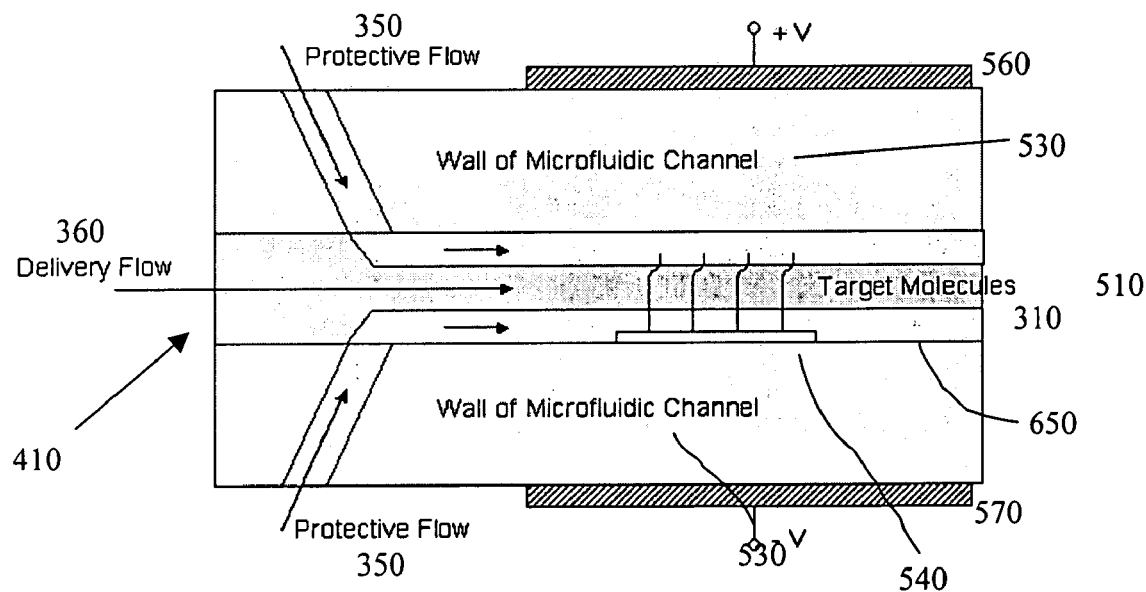
Figure 6:
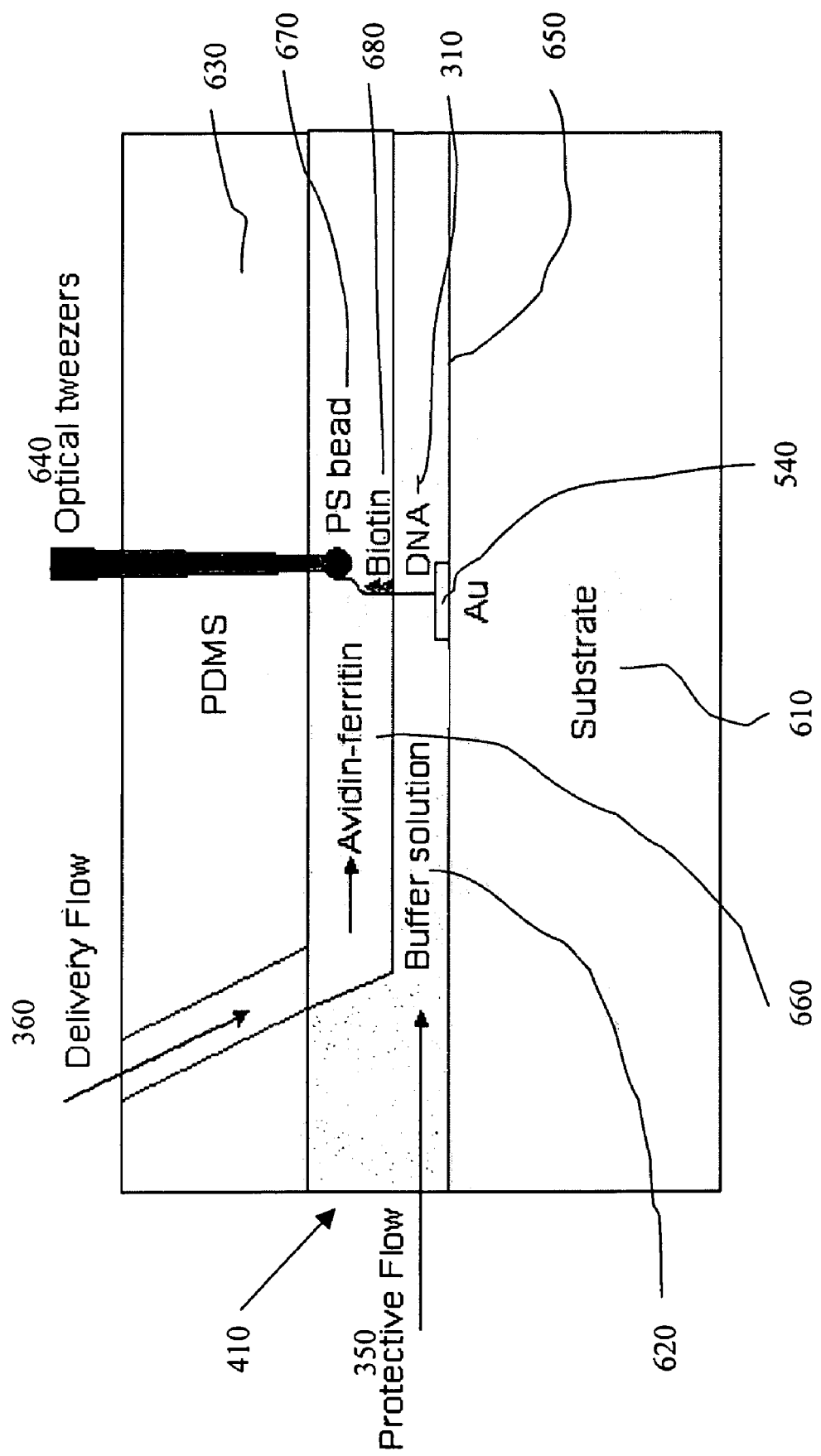
FIG. 6 illustrates a microfluidic system that includes a single protective flow 350 and a delivery flow 360 that is located in the top portion of a microfluidic channel 410, above the protective flow 350.

Accordingly, in another embodiment, provided herein is a method for contacting a first molecule with a second molecule within a microfluidic device, including delivering through the microfluidic device, at least one hydrodynamically focused delivery flow having the first molecule and/or the second molecule suspended therein, and at least one protective flow that at least partially inhibits the second molecule from contacting a surface of the microfluidic device. The protective flow(s) typically run parallel and restrict the flow of the delivery flow, as shown in FIGS. 5A, 5B, and 6. The first molecule can be immobilized on the surface of the microfluidic device and stretched, before and while it is contacted with the second molecule in the delivery flow.

The protective flow can block at least some or all detectable non-specific binding of the second molecule to a surface of the microfluidic device. Furthermore, the protective flow typically inhibits the delivery flow from contacting at least one surface of the microfluidic device. In addition, the protective flow typically includes an undetectable amount of the first molecule or the second molecule. A second protective flow that at least partially inhibits the second molecule from contacting a second surface of the microfluidic device can also be provided.

In one specific example, a method is provided to inhibit non-specific binding in a microfluidic device, including
a) immobilizing a first molecule on a surface of the microfluidic device;
b) stretching the first molecule;
c) delivering at least one protective flow through the microfluidic device; and
d) delivering through the microfluidic device, at least one hydrodynamically-focused delivery flow having a second molecule suspended therein, wherein the protective flow inhibits the delivery flow from contacting the surface of the microfluidic device as the first molecule binds to the second molecule.

Biomolecules or particles for bioreactions or specific bindings are delivered by one or more separate laminar flows (delivery flows) into a microfluidic channel. Delivery flows, such as hydrodynamically focused delivery flows as disclosed herein, are separated from the specific surfaces of the channel by protective flows. It has been demonstrated that two adjacent laminar flows containing different molecules, will not mix. For these aspects, target biomolecules are typically immobilized in a channel through various linkers as is known in the art, (e.g. DNA with one end immobilized on a surface and the other linked with the target biomolecules).

A first molecule, such as a target biomolecule, is held in position in the delivery flow by stretching the target biomolecule. This stretching can be the result of forces known in the art, such as electrical fields, magnetic fields (with magnetic nanoparticles attached to the molecules) or optical manipulation (with polystyrene beads attached to the molecules). For example, methods disclosed herein for aligning molecules can be used to stretch molecules.

The protective flow can surround a delivery flow to focus the delivery flow, thereby providing for more efficient molecule delivery of a second molecule to the target molecule (i.e. first molecule), as disclosed above related to hydrodynamic focusing methods. Furthermore, the protective flow at least partially inhibits, and in some aspects completely blocks, the delivery flow, and molecules suspended in the delivery flow, from contacting a surface of the microfluidic device. In addition, methods herein can include a second protective flow, wherein the first and second protective flows are adjacent to opposite surfaces of a delivery flow. It has been demonstrated that two adjacent laminate flows containing different molecules will not mix.

A wide variety of solutions can be delivered in the protective flows, provided that the solutions do not increase background values. For example, a protective flow can contain a buffer solution, and optionally can include blocking agents, for example BSA. It will be understood that a specific formulation of a protective flow depends on the specific reaction being performed. For example, standard ELISA concentrations of BSA blocking can be used for methods involving antibody-antigen binding.

With reference to FIGS. 5-7, target molecules (e.g. nucleic acid molecules 310) are immobilized at one end on an inner surface 650 of a microfluidic channel 410 by, for example, to a gold coated region 540 of the surface 650 of the channel 410 by thiol-gold interaction. The other end of the nucleic acid molecules 310 is associated with a magnetic molecule 510, such as a magnetic nanoparticle (FIG. 5A) or a charged moiety (FIG. 5B). The magnetic nanoparticle or the charged moiety can be used to stretch the target nucleic acid molecule 310 strands under a magnetic field or an electrical field, respectfully. The magnetic field is generated by a magnet 520 which is held near one side of the microfluidic channel 410. As shown in FIG. 5B, an electrical field is generated by a power source 560, 570 that is used to provide a current across the microfluidic channel 410. A delivery flow 360 is confined to the center of the channel by the protective flows 350. Therefore, the active biomolecules or particles in the delivery flow 360 can only reach the center part of the target molecule 310 strand that is suspended in the center region of the channel 410. This helps to reduce contact, and therefore non-specific binding, to the surfaces of the channel 410 by biomolecules or particles in the delivery flow 360.

FIG. 6 illustrates a microfluidic system for performing an illustrative method provided herein that includes delivery of a protective flow to reduce non-specific binding to a surface in a labeling reaction. As discussed herein, these methods typically involve an immobilizing a molecule, such as a specific binding pair member, and delivery of a second specific binding pair member in a delivery flow, to the immobilized molecule. In the example provided in FIG. 6, a buffer solution 620 flows in a microfluidic channel 410 formed from a flat substrate 610 and a molded piece 630 made for example of PDMS. A nucleic acid molecule 310 is immobilized at one end on a surface 650, such as a gold surface, in the microfluidic channel 410. The other end of the nucleic acid molecule 310 is attached to a particle 670, such as a poly-styrene bead, which can be manipulated by optical tweezers 640. Several biotin moieties 680 are attached to the middle section of the nucleic acid molecule 310. Under the manipulation of optical tweezers 640, the nucleic acid molecule 310 is stretched, thereby causing the biotin moieties 680 to be suspended near the center of the channel. A delivery flow 360 that contains avidin-ferritin conjugates 660 (i.e. second molecules) is then introduced into the channel, but is confined to the upper (or center, if the geometry in FIGS. 5A and 5B is used) part of the channel. The bottom portion (i.e. substrate surface) of the channel is protected by the protective flow of a buffer solution 350. Accordingly, the avidin-ferritin conjugates 660 bind to the biotin-molecules 680 on the center segment of the suspended nucleic acid molecule.

To confirm that the avidin-ferritin conjugate 660 binding occurred, the substrate 610 can be rinsed and the channel 410 dried. After peeling off the PDMS piece 630, ferritin molecules 660 that are bound to the biotin moieties 680 on the nucleic acid molecule 310 are detected on a clean substrate surface 650.

The width and/or diameter of the protective flow can be controlled by changing the force used to produce the protective flow, by changing the pressure of an adjacent flow, or by changing the viscosity of the protective flow, as discussed above for delivery flows. The width or diameter of the one or more protective flows in the methods provided herein is typically less than 10 microns, and in certain examples is less than 5, 4, 3, 2, 1, and 0.5, microns (linear scale), but at least 0.2 microns (linear scale).

As indicated, the protective flows inhibit the delivery flow from contacting the surface of the microfluidic device as a first molecule binds to a second molecule. Typically, this inhibition is the result of the protective flows flowing between the delivery flow and the surface of a microfluidic channel. Therefore, the protective flow continues to flow as the first molecule binds the second molecule. The protective flow typically continues to flow through the binding reaction of the first molecule and the second molecule.

Protective flows can be used to inhibit non-specific binding to microchannel surfaces in virtually any binding reaction where it is desirable to block non-specific binding to a surface of a reaction microchannel. For example, protective flows can be used in labeling reactions, immunoassays and receptor/ligand binding assays. The use of protective flows in labeling reactions is illustrated in FIGS. 5A-5B and 6, as discussed above. Regarding the use of protective flows in immunoassays, an antibody can be immobilized on the surface of the microchannel and stretched. Then, a sample suspected of containing an antigen, such as a biological sample, can be delivered in a delivery flow to the antibody binding region of the antibody, wherein a protective flow separates the delivery flow from the surface. Regarding the use of protective flows in receptor/ligand binding reactions, a receptor can be immobilized on the surface of a microchannel and stretched. Then a sample suspected of containing a ligand, such as a biological sample, can be delivered in a delivery flow to the ligand binding region of the receptor, wherein a protective flow separates the delivery flow from the surface. As another example, a nucleic acid strand with binding agents at specific locations along the nucleic acid, can be reacted with gold nanoparticles such that the gold nanoparticles are focused away from the surface for further sample interrogation using scanning probe microscopy techniques.

The following general teachings provided further details regarding the methods, systems, apparatuses disclosed herein. One or more molecules analyzed in the methods provided herein can be labeled with a Raman label. With respect to nucleic acids, typically the nucleic acid molecules are labeled before they are attached to a particle in embodiments that utilize a restriction barrier. Some or all of the nucleotides of a nucleic acid molecule can be labeled. For example only purine residues of a nucleic acid molecule can be labeled with a Raman label. Methods for determining a nucleotide sequence can be repeated several times with different labeled copies of a nucleic acid molecule or with different strands of the nucleic acid molecule, to obtain addition and possibly complete sequence information.

A Raman label can be any organic or inorganic molecule, atom, complex or structure capable of producing a detectable Raman signal, including but not limited to synthetic molecules, dyes, naturally occurring pigments such as phycoerythrin, organic nanostructures such as $C_{60}$, buckyballs and carbon nanotubes or nanoprisms and nano-scale semiconductors such as quantum dots. Numerous examples of Raman labels are disclosed below. The skilled artisan will realize that such examples are not limiting, and that a Raman label can encompasses any organic or inorganic atom, molecule, compound or structure known in the art that can be detected by Raman spectroscopy.

Non-limiting examples of labels that can be used for Raman spectroscopy include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins and aminoacridine. Polycyclic aromatic compounds in general can function as Raman labels, as is known in the art. These and other Raman labels can be obtained from commercial sources (e.g., Molecular Probes, Eugene, Oreg.).

Other labels that can be of use include cyanide, thiol, chlorine, bromine, methyl, phosphorus and sulfur. Carbon nanotubes can also be of use as Raman labels. The use of labels in Raman spectroscopy is known (e.g., U.S. Pat. Nos. 5,306,403 and 6,174,677). The skilled artisan will realize that Raman labels should generate distinguishable Raman spectra when bound to different types of nucleotide.

Labels can be attached directly to a nucleotide or other biomolecule, or can be attached via various linker compounds. Raman labels that contain reactive groups designed to covalently react with other molecules, are commercially available (e.g., Molecular Probes, Eugene, Oreg.).

In many of the methods provided herein, a reaction chamber or reaction area of a channel contains an immobilized nucleic acid molecule and a deconstruction reagent, such as an exonuclease. The exonuclease catalyzes the sequential release of individual nucleotides from the free end of the nucleic acid molecule. As the individual nucleotides are released by the deconstruction reaction and enter solution, they move down the flow path past a SERS detection unit. The detection unit includes an excitation source, such as a laser, that emits an excitatory beam. The excitatory beam interacts with the released nucleotides, and/or labels attached to the released nucleotides, so that electrons are excited to a higher energy state. The Raman emission spectrum that results from the return of the electrons to a lower energy state is detected by a Raman spectroscopic detector, such as a spectrometer or a monochromator.

The released nucleotides are spatially separated from the nucleic acid molecule before detection by the detection unit. Spatial separation acts to increase the signal-to-noise ratio of the Raman detector by isolating the individual nucleotides.

In embodiments herein, the nucleic acid molecule is fixed in place, as by attachment to an immobilization structure, such as by being captured in a restriction barrier, and immersed in a microfluidic flow down a flow path that transports the released nucleotides away from the nucleic acid molecule and past a detection unit. In non-limiting examples, the microfluidic flow may result from a bulk flow of solvent past the nucleic acid molecule and down a flow path, for example, a microcapillary tube or an etched channel in a silicon, glass or other chip. In alternative embodiments, the bulk medium moves only slowly or not at all, but charged species within the solution (such as negatively charged nucleotides) move down a flow path comprising a channel or tube in response to an externally applied electrical field.

In the embodiments discussed above, the detection unit must be capable of distinguishing between the common nucleotides released from the nucleic acid molecule. At a minimum, the detection unit must be able to distinguish between nucleotides containing adenosine (A), guanosine (G), cytosine (C) and thymidine (T) for sequencing DNA molecules. If RNA is being sequenced, the detection unit must be able to distinguish between nucleotides containing A, G, C and uridine (U). With a single nucleic acid molecule per reaction chamber, it is not necessary that the detection unit be capable of quantifying the amounts of each nucleotide in solution, since the nucleotides move past the detection unit 18 one at a time.

The skilled artisan will realize that analysis of DNA, will result in the release of deoxyribonucleosides or deoxyribonucleotides, (including thymidine), while analysis of RNA will result in the release of ribonucleosides or ribonucleotides (including uridine). Although nucleoside monophosphates will generally be the form released by exonuclease activity, the embodiments are not limited to detection of any particular form of free nucleotide or nucleoside but encompass any monomer that may be released from a nucleic acid by the activity of a deconstruction reagent.

In some embodiments of the invention, a method disclosed herein can be performed in a micro-electro-mechanical system (MEMS). MEMS are integrated systems that include mechanical elements, sensors, actuators, and electronics. All of those components can be manufactured by known microfabrication techniques on a common chip, including a silicon-based or equivalent substrate (e.g., Voldman et al., *Ann. Rev. Biomed. Eng.* 1:401-425, 1999). The sensor components of MEMS can be used to measure mechanical, thermal, biological, chemical, optical and/or magnetic phenomena. The electronics can process the information from the sensors and control actuator components such pumps, valves, heaters, coolers, filters, etc. thereby controlling the function of the MEMS.

The electronic components of MEMS can be fabricated using integrated circuit (IC) processes (e.g., CMOS, Bipolar, or BICMOS processes). They can be patterned using photolithographic and etching methods known for computer chip manufacture. The micromechanical components can be fabricated using compatible "micromachining" processes that selectively etch away parts of the silicon wafer or add new structural layers to form the mechanical and/or electromechanical components.

Basic techniques in MEMS manufacture include depositing thin films of material on a substrate, applying a patterned mask on top of the films by photolithographic imaging or other known lithographic methods, and selectively etching the films. A thin film can have a thickness in the range of a few nanometers to 100 micrometers. Deposition techniques of use may include chemical procedures such as chemical vapor deposition (CVD), electrodeposition, epitaxy and thermal oxidation and physical procedures like physical vapor deposition (PVD) and casting.

In some embodiments of the invention, MEMS devices include various fluid filled compartments, such as microfluidic channels, nanochannels and/or microchannels. These and other components of the apparatus can formed as a single unit, for example in the form of a chip as known in semiconductor chips and/or microcapillary or microfluidic chips. Alternatively, an immobilization substrate, such as a metal coated porous silicon substrate, can be removed from a silicon wafer and attached to other components of an apparatus. Any materials known for use in such chips may be used in the disclosed apparatus, including silicon, silicon dioxide, silicon nitride, polydimethyl siloxane (PDMS), polymethylmethacrylate (PMMA), plastic, glass, quartz.

Techniques for batch fabrication of chips are well known in the fields of computer chip manufacture and/or microcapillary chip manufacture. Such chips may be manufactured by any method known in the art, such as by photolithography and etching, laser ablation, injection molding, casting, molecular beam epitaxy, dip-pen nanolithography, chemical vapor deposition (CVD) fabrication, electron beam or focused ion beam technology or imprinting techniques. Non-limiting examples include conventional molding with a flowable, optically clear material such as plastic or glass; photolithography and dry etching of silicon dioxide; electron beam lithography using polymethylmethacrylate resist to pattern an aluminum mask on a silicon dioxide substrate, followed by reactive ion etching. Known methods for manufacture of nanoelectromechanical systems may be used for certain embodiments of the invention. (See, e.g., Craighead, Science 290: 1532-36, 2000.) Various forms of microfabricated chips are commercially available from, e.g., Caliper Technologies Inc. (Mountain View, Calif.) and ACLARA BioSciences Inc. (Mountain View, Calif.).

In certain embodiments of the invention, part or all of the apparatus can be selected to be transparent to electromagnetic radiation at the excitation and emission frequencies used for Raman spectroscopy, such as glass, silicon, quartz or any other optically clear material. For fluid-filled compartments that may be exposed to various biomolecules, such as proteins, peptides, nucleic acids, nucleotides and the like, the surfaces exposed to such molecules may be modified by coating, for example to transform a surface from a hydrophobic to a hydrophilic surface and/or to decrease adsorption of molecules to a surface. Surface modification of common chip materials such as glass, silicon, quartz and/or PDMS is known in the art (e.g., U.S. Pat. No. 6,263,286). Such modifications may include, but are not limited to, coating with commercially available capillary coatings (Supelco, Bellafonte, Pa.), silanes with various functional groups such as polyethyleneoxide or acrylamide, or any other coating known in the art.

In certain aspects, the systems and apparatus provided herein are microfluidic devices that include a micromold. Techniques such as soft lithography and photolithography, which have been used in the semiconductor industry, can be used to fabricate micromold of microfluidic device. For example, designs of micromold can be drawn to scale using CAD software. The designs can then printed onto transparencies using a high-resolution printer to form a transparency mask. "Photoresist on Silicon" masters for micromolding can then prepared by standard photolithographic techniques using the transparency masks and a photoresist. These patterned masters can then silanized and used for micromolding with a silicone material such as poly(dimethyl siloxane) (PDMS). For example, PDMS precursor can be poured onto the silanized master and then cured. The cured PDMS containing the channel structure can then bonded to the supporting surface by applying pressure to enclose the channels. Typically, the microchannel pathways are approximately 100 microns in width and between about two centimeters and about three centimeters in length.

The substrate can also be prepared using standard lithographic techniques. For example, a photoresist can be deposited on substrate support surface and exposed through a mask. The exposed photoresist can be developed. A suitable heating element or substrate material can be deposited by, for example, sputter deposition. In one embodiment, a thin layer of titanium or chromium having a thickness of about 80 Å is deposited, followed by subsequent deposition of a thin layer of gold having a thickness of about 240 Å. The photoresist is then lifted off of substrate support surface, thereby providing a substrate and/or heating element on the substrate support surface.

The nucleotide is detected in the methods provided herein, by SERS using a Raman detection unit. The Raman detection unit includes a laser excitation and a wavelength selective detector. The light source is typically a laser light, as known in the art and discussed in more detail herein. Light from the light source is projected at the first specific binding pair member and detected by the detector.

The detection unit includes an excitation source, such as a laser, and a Raman spectroscopy detector. The excitation source illuminates the reaction chamber or channel with an excitation beam. The excitation beam interacts with the first specific binding pair member, resulting in the excitation of electrons to a higher energy state. As the electrons return to a lower energy state, they emit a Raman emission signal that is detected by the Raman detector.

Data can be collected from a detector, such as a spectrometer or a monochromator array and provided to an information processing and control system. The information processing and control system can perform standard procedures known in the art, such as subtraction of background signals. Furthermore, the information processing and control system can analyze the data to determine nucleotide sequence information from detected signals and the temporal relationship of these signals.

The nucleotide detection and/or sequencing reaction of methods provided herein involves binding of a deconstruction reagent to the free end of the nucleic acid molecule and removal of nucleotides one at a time. In certain embodiments the reaction may be catalyzed by an enzyme, such as an exonuclease. The embodiments are not limited by the type of exonuclease that may be used. Non-limiting examples of exonucleases of potential use include *E. coli* exonuclease I, III, V or VII, Bal exonuclease, mung bean exonuclease, S1 nuclease, *E. coli* DNA polymerase I holoenzyme or Klenow fragment, RecJ, exonuclease T, T4 or T7 DNA polymerase, Taq polymerase, exonuclease T7 gene 6, snake venom phosphodiesterase, spleen phosphodiesterase, *Thermococcus litoralis* DNA polymerase, *Pyrococcus* sp. GB-D DNA polymerase, lambda exonuclease, *S. aureus* micrococcal nuclease, DNase I, ribonuclease A, Ti micrococcal nuclease, or other exonucleases known in the art. Exonucleases are available from commercial sources such as New England Biolabs (Beverly, Mass.), Amersham Pharmacia Biotech (Piscataway, N.J.), Promega (Madison, Wis.), Sigma Chemicals (St. Louis, Mo.) or Boehringer Mannheim (Indianapolis, Ind.).

The skilled artisan will realize that enzymes with exonuclease activity have various properties, for example, they can remove nucleotides from the 5' end, the 3' end, or either end of the nucleic acid molecule. They can show specificity for RNA, DNA or both RNA and DNA. Their activity may depend on the use of either single or double-stranded nucleic acids. They may be differentially affected by various characteristics of the reaction medium, such as salt, temperature, pH, or divalent cations. These and other properties of the various exonucleases and polymerases are known in the art.

The skilled artisan will realize that the rate of exonuclease activity may be manipulated to coincide with the optimal rate of analysis of nucleotides by the detection unit. Various methods are known for adjusting the rate of exonuclease activity, including adjusting the temperature, pressure, pH, salt concentration or divalent cation concentration in the reaction chamber. Methods of optimization of exonuclease activity are known in the art.

Surfaces of the reaction chamber, reaction area, and/or flow path that are opposite the detection unit can be coated with silver, gold, platinum, copper, aluminum or other materials that are relatively opaque to the detection unit. In that position, the opaque material is available to enhance the Raman or other signal, for example by surface enhanced Raman spectroscopy, while not interfering with the function of the detection unit. Alternatively, the reaction chamber and/or flow path can contain a mesh comprising silver, gold, platinum, copper or aluminum. The skilled artisan will realize that in embodiments involving a flow path, the nucleotides will generally be detected while they are in the flow path. In embodiments without a flow path, the nucleotides will be detected in the reaction chamber.

The reaction chamber can have an internal volume of about 1 picoliter, about 2 picoliters, about 5 picoliters, about 10 picoliters, about 20 picoliters, about 50 picoliters, about 100 picoliters, about 250 picoliters, about 500 picoliters, about 1 nanoliter, about 2 nanoliters, 5 nanoliters, about 10 nanoliters, about 20 nanoliters, about 50 nanoliters, about 100 nanoliters, about 250 nanoliters, about 500 nanoliters, about 1 microliter, about 2 microliters, about 5 microliters, about 10 microliters, about 20 microliters, about 50 microliters, about 100 microliters, about 250 microliters, about 500 microliters, or about 1 milliliter.

Free nucleotides after release from the restriction barrier are moved down a flow path past the detection unit. Non-limiting example of techniques for transport of free nucleotides includes microfluidic techniques. The flow path can comprise a microcapillary (available, e.g., from ACLARA BioSciences Inc., Mountain View, Calif.) or a liquid integrated circuit (e.g., Caliper Technologies Inc., Mountain View, Calif.). Such microfluidic platforms require only nanoliter volumes of sample.

In certain embodiments, the free nucleotides to be detected move down the flow path by bulk flow of solvent. In other embodiments, microcapillary electrophoresis is used to transport free nucleotides down the flow path and past the detection unit. Microcapillary electrophoresis generally involves the use of a thin capillary or channel that may or may not be filled with a particular separation medium. Electrophoresis of appropriately charged molecular species, such as negatively charged nucleotides, occurs in response to an imposed electrical field, negative on the reaction chamber side of the apparatus and positive on the detection unit side. Although electrophoresis is often used for size separation of a mixture of components that are simultaneously added to the microcapillary, it can also be used to transport similarly sized nucleotides that are sequentially added to the flow path. Because the purine nucleotides (A, G) are larger than the pyrimidine nucleotides (C, T, U) and would therefore migrate more slowly, the length of the flow path and corresponding transit time past the detector unit should be kept to a minimum to prevent differential migration from mixing up the order of nucleotides released from the nucleic acid. Alternatively, the separation medium filling the microcapillary may be selected so that the migration rates of purine and pyrimidine nucleotides down the flow path are similar or identical. Methods of microcapillary electrophoresis have been disclosed, for example, by Woolley and Mathies (*Proc. Natl. Acad. Sci. USA* 91:11348-352, 1994).

In various embodiments provided herein, nucleic acid molecules to be sequenced or otherwise analyzed, or other biomolecules, can be attached to a solid surface (or immobilized). Immobilization of nucleic acid molecules can be achieved by a variety of methods involving either non-covalent or covalent attachment between the nucleic acid molecule and the surface. For example, immobilization can be achieved by coating a surface with streptavidin or avidin and the subsequent attachment of a biotinylated nucleic acid 13, 102 (Holmstrom et al., *Anal. Biochem.* 209:278-283, 1993). Immobilization can also occur by coating a silicon, glass or other surface 14, 103 with poly-L-Lys (lysine) or poly L-Lys, Phe (phenylalanine), followed by covalent attachment of either amino- or sulfhydryl-modified nucleic acids using bifunctional crosslinking reagents (Running et al., *BioTechniques* 8:276-277, 1990; Newton et al., *Nucleic Acids Res.* 21:1155-62, 1993). Amine residues can be introduced onto a surface 14, 103 through the use of aminosilane for crosslinking.

Immobilization can take place by direct covalent attachment of 5'-phosphorylated nucleic acids to chemically modified surfaces 14, 103 (Rasmussen et al., *Anal. Biochem.* 198: 138-142, 1991). The covalent bond between the nucleic acid 13, 102 and the surface 14, 103 is formed by condensation with a water-soluble carbodiimide. This method facilitates a predominantly 5'-attachment of the nucleic acids 13, 102 via their 5'-phosphates.

DNA is commonly bound to glass by first silanizing the glass surface, then activating with carbodiimide or glutaraldehyde. Alternative procedures can use reagents such as 3-glycidoxypropyltrimethoxysilane (GOP) or aminopropyltrimethoxysilane (APTS) with DNA linked via amino linkers incorporated either at the 3' or 5' end of the molecule. DNA can be bound directly to membrane surfaces using ultraviolet radiation. Other non-limiting examples of immobilization techniques for nucleic acids are disclosed in U.S. Pat. Nos. 5,610,287, 5,776,674 and 6,225,068.

The type of surface to be used for immobilization of the nucleic acid is not limiting. In various embodiments, the immobilization surface can be magnetic beads, non-magnetic beads, a planar surface, a pointed surface, or any other conformation of solid surface comprising almost any material, so long as the material is sufficiently durable and inert to allow the nucleic acid sequencing reaction to occur. Non-limiting examples of surfaces that can be used include glass, silica, silicate, PDMS, silver or other metal coated surfaces, nitrocellulose, nylon, activated quartz, activated glass, polyvinylidene difluoride (PVDF), polystyrene, polyacrylamide, other polymers such as poly(vinyl chloride), poly(methyl methacrylate) or poly(dimethyl siloxane), and photopolymers which contain photoreactive species such as nitrenes, carbenes and ketyl radicals capable of forming covalent links with nucleic acid molecules 13, 102 (See U.S. Pat. Nos. 5,405,766 and 5,986,076).

Bifunctional cross-linking reagents can be of use in various embodiments, such as attaching a nucleic acid molecule to a surface. The bifunctional cross-linking reagents can be divided according to the specificity of their functional groups, e.g., amino, guanidino, indole, or carboxyl specific groups. Of these, reagents directed to free amino groups are popular because of their commercial availability, ease of synthesis and the mild reaction conditions under which they can be applied. Exemplary methods for cross-linking molecules are disclosed in U.S. Pat. Nos. 5,603,872 and 5,401,511. Cross-linking reagents include glutaraldehyde (GAD), bifunctional oxirane (OXR), ethylene glycol diglycidyl ether (EGDE), and carbodiimides, such as 1-ethyl-3-(3-dimethylaminopropyl) carbodiimide (EDC).

What is claimed is:

1. An apparatus comprising, a first channel comprising a restriction barrier comprising a first angled wall and a second angled wall positioned relative to the first angled wall to form a first opening at least 1 micron in width or diameter and a second opening less than 10 microns in width or diameter, wherein the first opening has a greater width or diameter than the second opening, further comprising a laser light source and a series of lenses to form a gradient force optical trap operable as optical tweezers configured to capture a particle downstream of the restriction barrier and release it upstream of the restriction barrier, a light source and a Raman detector to detect a single molecule by a surface enhanced Raman spectroscopy, the first channel being in optical communication with the light source and the Raman detector.

2. The apparatus of claim 1 wherein the second opening is less than 1 micron in width or diameter.

3. The apparatus of claim 1, further comprising a second channel forming a junction with the first channel.

4. The apparatus of claim 1, wherein the restriction barrier is located upstream of the junction of the first channel and the second channel.

5. The apparatus of claim 1, wherein the gradient force optical trap is positioned downstream of the junction of the first channel and the second channel.

6. The apparatus of claim 1, wherein the light source is positioned downstream from the restriction barrier and upstream from the gradient force optical trap.

7. The apparatus of claim 1, wherein the Raman detector is configured to detect a single nucleotide by surface enhanced Raman spectroscopy.

8. A system comprising: a) a light source; b) a Raman detector configured to detect a single molecule by a surface enhanced Raman spectroscopy and c) a first channel in optical communication with the light source and the detector, wherein the first channel comprises a restriction barrier within the first channel, the restriction barrier comprising a plurality of walls to restrain movement of a single particle upstream of light emitted by the light source, wherein the particle has a diameter between 0.1 and 20 microns, wherein the first channel is separate and distinct from the restriction barrier such that there is a gap between a wall of the channel and the restriction barrier.

9. The system of claim 8, wherein the restriction barrier comprises a first angled wall and a second angled wall positioned relative to the first angled wall to form a first opening at least 1 micron in width or diameter and a second opening less than 10 microns in width or diameter, wherein the first opening has a greater width or diameter than the second opening.

10. The system of claim 9, further comprising a second channel forming a junction with the first channel.

11. The system of claim 10 wherein the restriction barrier is located upstream of the junction of the first channel and the second channel.

12. The system of claim 11, further comprising a gradient force optical trap positioned downstream of the junction of the first channel and the second channel.

13. The system of claim 12, wherein the light source is positioned downstream from the restriction barrier and upstream from the gradient force optical trap.

14. The system of claim 8, wherein a portion of a flow path in optical communication with the detection light source is coated with silver, gold, platinum, copper or aluminum.

15. The system of claim 8, wherein the Raman detector is configured to detect a single nucleotide by surface enhanced Raman spectroscopy.

16. An apparatus comprising a first channel having a restriction barrier within the channel, the restriction barrier comprising a first angled wall and a second angled wall positioned relative to the first angled wall to form a first opening large enough to capture a single particle and a second opening small enough to prevent passage of the particle but large enough to allow passage of a biomolecule, wherein the first opening is at least 100 nm wide and the second opening is less than 10 microns wide, and wherein the first opening has a greater width or diameter than the second opening, further comprising a laser light source and a series of lenses to form a gradient force optical trap operable as optical tweezers configured to capture a particle downstream of the restriction barrier and release it upstream of the restriction barrier, wherein the first channel is separate and distinct from the restriction barrier such that there is a gap between a wall of the channel and the restriction barrier.

17. The apparatus of claim 16, further comprising a second channel forming a junction with the first channel.

18. The apparatus of claim 16, wherein the restriction barrier is located upstream of the junction of the first channel and the second channel.

19. The apparatus of claim 16, wherein the gradient force optical trap is positioned downstream of the junction of the first channel and the second channel.

20. The apparatus of claim 16, wherein the light source is positioned downstream from the restriction barrier and upstream from the gradient force optical trap.

21. The apparatus of claim 16, further comprising a Raman detector configured to detect a single nucleotide by surface enhanced Raman spectroscopy.

* * * * *

SEQUENCE LISTING

<160> NUMBER OF SEQ ID NOS: 1

<210> SEQ ID NO 1
<211> LENGTH: 13
<212> TYPE: DNA
<213> ORGANISM: Artificial Sequence
<220> FEATURE:
<223> OTHER INFORMATION: Synthetized Construct
<220> FEATURE:
<221> NAME/KEY: misc_feature
<222> LOCATION: 13

<400> SEQUENCE: 1
atcgatacga tcg                                                          13